(12) United States Patent
Zhang et al.

(10) Patent No.: US 12,358,927 B2
(45) Date of Patent: Jul. 15, 2025

(54) IRAK4 INHIBITOR CRYSTAL AND PREPARATION METHOD THEREFOR

(71) Applicant: CHIA TAI TIANQING PHARMACEUTICAL GROUP CO., LTD., Lianyungang (CN)

(72) Inventors: Yang Zhang, Shanghai (CN); Jianfei Wang, Shanghai (CN); Haizhong Tan, Shanghai (CN); Yuhai Xing, Shanghai (CN); Jian Li, Shanghai (CN); Shuhui Chen, Shanghai (CN)

(73) Assignee: Chia Tai Tianqing Pharmaceutical Group Co., Inc., Lianyungang (CN)

( * ) Notice: Subject to any disclaimer, the term of this patent is extended or adjusted under 35 U.S.C. 154(b) by 463 days.

(21) Appl. No.: 17/792,792

(22) PCT Filed: Jan. 21, 2021

(86) PCT No.: PCT/CN2021/073152
§ 371 (c)(1),
(2) Date: Jul. 14, 2022

(87) PCT Pub. No.: WO2021/147968
PCT Pub. Date: Jul. 29, 2021

(65) Prior Publication Data
US 2023/0060905 A1 Mar. 2, 2023

(30) Foreign Application Priority Data

Jan. 21, 2020 (CN) .......................... 202010071573.9
Jul. 30, 2020 (CN) .......................... 202010753615.7

(51) Int. Cl.
*C07D 513/04* (2006.01)

(52) U.S. Cl.
CPC ........ *C07D 513/04* (2013.01); *C07B 2200/13* (2013.01)

(58) Field of Classification Search
None
See application file for complete search history.

(56) References Cited

U.S. PATENT DOCUMENTS 7,544,799 B2   6/2009   Zimmermann et al.
9,242,922 B2   1/2016   Takada et al.
(Continued)

FOREIGN PATENT DOCUMENTS

CN   106232122 A   12/2016
EA      019342 B1    2/2012
(Continued)

OTHER PUBLICATIONS

Atipamula et al., Cryst. Growth Des. 2012, 12, 5, 2147-2152 (Year: 2012).*
(Continued)

*Primary Examiner* — Jeffrey S Lundgren
*Assistant Examiner* — Anthony Joseph Seitz
(74) *Attorney, Agent, or Firm* — NIXON PEABODY LLP

(57) ABSTRACT

Provided are a crystal of a compound of formula (I), salt thereof, a crystal of the salt thereof, and a preparation method for the crystal. Also comprised are applications of the compound and the crystal in preparation of drugs for treating IRAK4-related diseases.

(Continued)

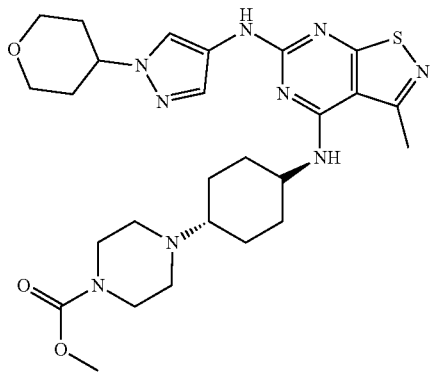

(I)

6 Claims, 9 Drawing Sheets

(56) References Cited

U.S. PATENT DOCUMENTS

| | | | |
|---|---|---|---|
| 9,308,205 | B2 | 4/2016 | Becker et al. |
| 9,518,065 | B2 | 12/2016 | Romero |
| 11,459,337 | B2 * | 10/2022 | Zhang ............ C07D 513/04 |
| 2015/0094305 | A1 | 4/2015 | Romero |
| 2021/0269456 | A1 | 9/2021 | Zhang |

FOREIGN PATENT DOCUMENTS

| | | |
|---|---|---|
| RU | 2208012 C2 | 7/2003 |
| RU | 2523279 C2 | 7/2014 |
| RU | 2016110852 A | 10/2017 |
| WO | WO 2017/004133 A1 | 1/2017 |
| WO | WO 2017/205766 A1 | 11/2017 |
| WO | WO 2020/001449 A1 | 1/2020 |

OTHER PUBLICATIONS

Bastin et al. "Salt selection and optimisation procedures for pharmaceutical new chemical entities." Organic Process Research & Development, 4.5, Jul. 19, 2000, pp. 427-435.

Sarma et al. "Solid forms of pharmaceuticals: Polymorphs, salts and cocrystals." Korean Journal of Chemical Engineering 28.2, Feb. 2011, pp. 315-322.

Caira. "Crystalline polymorphism of organic compounds." Topics in Current Chemistry, 198, (1998) pp. 163-208.

Gupta et al. "Salts of therapeutic agents: chemical, physicochemical, and biological considerations." Molecules, 23.7, (2018) pp. 1-15.

Supplementary Partial European Search Report issued in EP21743925 on Jan. 4, 2024.

International Search Report in International Patent Application No. PCT/CN2021/073152, mailed Mar. 31, 2021 (6 pages w/English translation).

Aaltonen et al. "Solid form screening—a review." European Journal of Pharmaceutics and Biopharmaceutics, 71(1): pp. 23-37 (2009).

* cited by examiner

IRAK4 INHIBITOR CRYSTAL AND PREPARATION METHOD THEREFOR

CROSS-REFERENCE TO RELATED APPLICATIONS

The present application is a U.S. National Stage Entry of International Application No. PCT/CN2021/073152 filed on Jan. 21, 2021, which claims the benefit and priority to Chinese Patent Application No. CN202010071573.9 filed with China National Intellectual Property Administration on Jan. 21, 2020 and Chinese Patent Application No. CN202010753615.7 filed with China National Intellectual Property Administration on Jul. 30, 2020, which are incorporated herein by reference in their entireties.

TECHNICAL FIELD

The present application relates to a crystalline form of a compound of formula (I), a salt thereof, a crystalline form of the salt thereof, and a method for preparing the crystalline form, in particular to the crystalline form of the compound of formula (I), a compound of formula (II) and a crystalline form thereof, a crystalline form of a compound of formula (III), a crystalline form of a compound of formula (IV), a crystalline form of a compound of formula (V), a crystalline form of a compound of formula (VI) and a method for preparing the crystalline forms, and also relates to use of the compound and the crystalline form in preparing a medicament for treating IRAK4-related diseases.

BACKGROUND

Interleukin-1 receptor associated kinase 4 (IRAK4) is a serine/threonine-specific protein kinase, a member of tyrosine-like kinase (TLK) family, and a key node in the innate immune response involving interleukin-1, 18 and 33, and toll-like receptors. After extracellular signal molecules bind to interleukin receptors or toll-like receptors, proteins are recruited to form a MyD88:IRAK4:IRAK1/2 complex, leading to IRAK1/2 phosphorylation which mediates a series of downstream signaling. Thus p38, INK, and NF-κB signaling pathways are activated, eventually promoting the expression of proinflammatory cytokines. Clinical pathology studies have shown that individuals with IRAK4 mutations have resistance against chronic lung disease and inflammatory bowel disease. IRAK4 deficiency is not lethal in itself, and the individuals can survive to adulthood with a reduced risk of infection over age. Therefore, IRAK4 becomes an important therapeutic target attracting extensive research and development interest.

SUMMARY

In one aspect, the present application provides a salt of a compound of formula (I), and the salt is selected from the group consisting of hydrochloride, sulfate, methanesulfonate, maleate and p-methylbenzenesulfonate

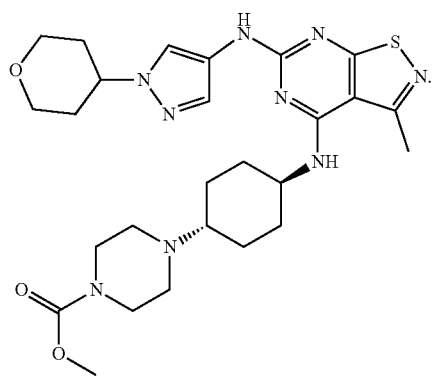

In another aspect, the present application provides a crystalline form of the hydrochloride of the compound of formula (I), a crystalline form of the sulfate of the compound of formula (I), a crystalline form of the methanesulfonate of the compound of formula (I), a crystalline form of the maleate of the compound of formula (I), or a crystalline form of the p-methylbenzenesulfonate of the compound of formula (I).

In another aspect, the present application provides a compound of formula (II),

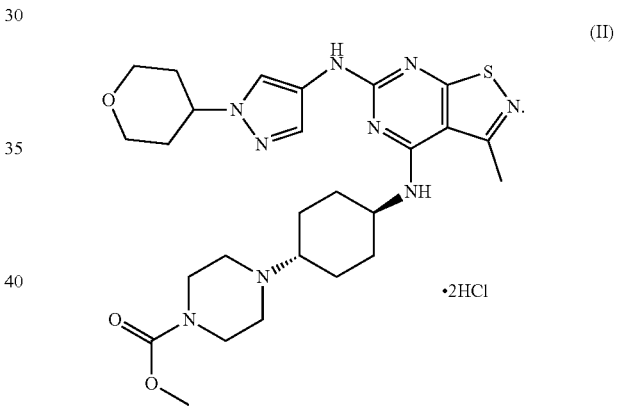

In another aspect, the present application also provides a crystalline form of the compound of formula (II).

In another aspect, the present application also provides a crystalline form A of the compound of formula (II) having characteristic diffraction peaks in an X-ray powder diffraction pattern using Cu Kα radiation at the following 2θ: 6.25±0.20°, 16.15±0.20° and 21.79±0.20°.

In some embodiments of the present application, the aforementioned crystalline form A of the compound of formula (II) has characteristic diffraction peaks in an X-ray powder diffraction pattern at the following 2θ: 6.25±0.20°, 12.58±0.20°, 14.33±0.20°, 16.15±0.20°, 20.00±0.20° and 21.79±0.20°.

In some embodiments of the present application, the aforementioned crystalline form A of the compound of formula (II) has characteristic diffraction peaks in an X-ray powder diffraction pattern at the following 2θ: 6.25±0.20°, 12.58±0.20°, 14.33±0.20°, 16.15±0.20°, 20.00±0.20°, 21.53±0.20° and 21.79±0.20°.

In some embodiments of the present application, the aforementioned crystalline form A of the compound of formula (II) has characteristic diffraction peaks in an X-ray powder diffraction pattern using Cu Kα radiation at the following 2θ: 6.25±0.20°, 12.58±0.20°, 14.33±0.20°, 16.15±0.20°, 20.00±0.20°, 20.57±0.20°, 21.79±0.20° and 28.02±0.20°.

In some embodiments of the present application, the aforementioned crystalline form A of the compound of formula (II) has characteristic diffraction peaks in an X-ray powder diffraction pattern using Cu Kα radiation at the following 2θ: 6.25±0.20°, 11.95±0.20°, 12.58±0.20°, 14.33±0.20°, 16.15±0.20°, 19.46±0.20°, 20.00±0.20°, 20.57±0.20°, 21.79±0.20°, 23.87±0.20°, 27.71±0.20° and 28.02±0.20°.

In some embodiments of the present application, the aforementioned crystalline form A of the compound of formula (II) has characteristic diffraction peaks in an X-ray powder diffraction pattern using Cu Kα radiation at the following 2θ: 6.25±0.20°, 8.06±0.20°, 9.29±0.20°, 11.95±0.20°, 12.58±0.20°, 14.33±0.20°, 16.15±0.20°, 19.46±0.20°, 20.00±0.20°, 20.57±0.20°, 21.53±0.20°, 21.79±0.20°, 27.71±0.20° and 28.02±0.20°.

In some embodiments of the present application, the aforementioned crystalline form A of the compound of formula (II) has characteristic diffraction peaks in an X-ray powder diffraction pattern using Cu Kα radiation at the following 2θ: 6.25±0.20°, 8.06±0.20°, 9.29±0.20°, 11.95±0.20°, 12.58±0.20°, 14.33±0.20°, 16.41±0.20°, 19.46±0.20°, 20.00±0.20°, 20.57±0.20°, 21.53±0.20°, 21.79±0.20°, 27.71±0.20° and 28.02±0.20°.

In some embodiments of the present application, the aforementioned crystalline form A of the compound of formula (II) has characteristic diffraction peaks in an X-ray powder diffraction pattern using Cu Kα radiation at the following 2θ: 6.25±0.20°, 8.06±0.20°, 9.29±0.20°, 11.95±0.20°, 12.58±0.20°, 14.33±0.20°, 16.15±0.20°, 16.41±0.20°, 19.46±0.20°, 20.00±0.20°, 20.57±0.20°, 21.53±0.20°, 21.79±0.20°, 27.71±0.20° and 28.02±0.20°.

In some embodiments of the present application, the aforementioned crystalline form A of the compound of formula (II) has characteristic diffraction peaks in an X-ray powder diffraction pattern using Cu Kα radiation at the following 2θ: 6.25±0.20°, 11.95±0.20°, 12.58±0.20°, 14.33±0.20°, 16.15±0.20°, 19.46±0.20°, 20.00±0.20°, 20.57±0.20°, 21.79±0.20°, 23.87±0.20°, 28.02±0.20° and 30.81±0.20°.

In some embodiments of the present application, the aforementioned crystalline form A of the compound of formula (II) has characteristic diffraction peaks in an X-ray powder diffraction pattern using Cu Kα radiation at the following 2θ: 6.250, 11.950, 12.580, 14.330, 16.150, 16.410, 18.200, 18.750, 19.460, 20.000, 20.570, 21.530, 21.790, 23.110, 23.870, 24.310, 25.260, 26.140, 27.710, 28.020, 28.500, 30.060, 30.810 and 33.210.

In some embodiments of the present application, the aforementioned crystalline form A of the compound of formula (II) has characteristic diffraction peaks in an X-ray powder diffraction pattern using Cu Kα radiation at the following 2θ: 6.25±0.20°, 11.95±0.20°, 12.58±0.20°, 14.33±0.20°, 16.15±0.20°, 16.41±0.20°, 18.20±0.20°, 18.75±0.20°, 19.46±0.20°, 20.00±0.20°, 20.57±0.20°, 21.53±0.20°, 21.79±0.20°, 23.11±0.20°, 23.87±0.20°, 24.31±0.20°, 25.26±0.20°, 26.14±0.20°, 27.71±0.20°, 28.02±0.20°, 28.50±0.20°, 30.06±0.20°, 30.81±0.20° and 33.21±0.20°.

In some embodiments of the present application, the aforementioned crystalline form A of the compound of formula (II) has characteristic diffraction peaks in an X-ray powder diffraction pattern using Cu Kα radiation at the following 2θ: 6.25±0.20°, 8.06±0.20°, 9.29±0.20°, 11.95±0.20°, 12.58±0.20°, 14.33±0.20°, 16.15±0.20°, 18.20±0.20°, 18.75±0.20°, 19.46±0.20°, 20.00±0.20°, 20.57±0.20°, 21.53±0.20°, 21.79±0.20°, 23.11±0.20°, 23.87±0.20°, 24.31±0.20°, 25.26±0.20°, 26.14±0.20°, 27.71±0.20°, 28.02±0.20°, 28.50±0.20°, 30.06±0.20°, 30.81±0.20° and 33.21±0.20°.

In some embodiments of the present application, the aforementioned crystalline form A of the compound of formula (II) has characteristic diffraction peaks in an X-ray powder diffraction pattern using Cu Kα radiation at the following 2θ: 6.25±0.20°, 8.06±0.20°, 9.29±0.20°, 11.95±0.20°, 12.58±0.20°, 14.33±0.20°, 16.41±0.20°, 18.20±0.20°, 18.75±0.20°, 19.46±0.20°, 20.00±0.20°, 20.57±0.20°, 21.53±0.20°, 21.79±0.20°, 23.11±0.20°, 23.87±0.20°, 24.31±0.20°, 25.26±0.20°, 26.14±0.20°, 27.71±0.20°, 28.02±0.20°, 28.50±0.20°, 30.06±0.20°, 30.81±0.20° and 33.21±0.20°.

In some embodiments of the present application, the aforementioned crystalline form A of the compound of formula (II) has characteristic diffraction peaks in an X-ray powder diffraction pattern using Cu Kα radiation at the following 2θ: 6.25±0.20°, 8.06±0.20°, 9.29±0.20°, 11.95±0.20°, 12.58±0.20°, 14.33±0.20°, 16.15±0.20°, 16.41±0.20°, 18.20±0.20°, 18.75±0.20°, 19.46±0.20°, 20.00±0.20°, 20.57±0.20°, 21.53±0.20°, 21.79±0.20°, 23.11±0.20°, 23.87±0.20°, 24.31±0.20°, 25.26±0.20°, 26.14±0.20°, 27.71±0.20°, 28.02±0.20°, 28.50±0.20°, 30.06±0.20°, 30.81±0.20° and 33.21±0.20°.

In some embodiments of the present application, the aforementioned crystalline form A of the compound of formula (II) has characteristic diffraction peaks in an X-ray powder diffraction pattern using Cu Kα radiation at the following 2θ: 6.25±0.20°, 8.06±0.20°, 9.29±0.20°, 11.95±0.20°, 12.58±0.20°, 14.33±0.20°, 16.15±0.20°, 16.41±0.20°, 18.20±0.20°, 18.75±0.20°, 19.46±0.20°, 20.00±0.20°, 20.57±0.20°, 21.53±0.20°, 21.79±0.20°, 23.11±0.20°, 23.87±0.20°, 24.31±0.20°, 25.26±0.20°, 26.14±0.20°, 27.71±0.20°, 28.02±0.20°, 28.50±0.20°, 30.06±0.20°, 30.81±0.20° and 33.21±0.20°.

In some embodiments of the present application, the aforementioned crystalline form A of the compound of formula (II) has characteristic diffraction peaks in an X-ray powder diffraction pattern using Cu Kα radiation at the following 2θ: 6.25±0.20°, 8.06±0.20°, 9.29±0.20°, 11.50±0.20°, 11.95±0.20°, 12.58±0.20°, 14.33±0.20°, 16.15±0.20°, 16.41±0.20°, 18.20±0.20°, 18.75±0.20°, 19.46±0.20°, 20.00±0.20°, 20.57±0.20°, 21.53±0.20°, 21.79±0.20°, 23.11±0.20°, 23.87±0.20°, 24.31±0.20°, 25.26±0.20°, 26.14±0.20°, 26.70±0.20°, 27.71±0.20°, 28.02±0.20°, 28.50±0.20°, 29.09±0.20°, 30.06±0.20°, 30.81±0.20°, 32.39±0.20°, 33.21±0.20° and 33.71±0.20°.

The present application provides a crystalline form A of a compound of formula (II) comprising 3, 4, 5, 6, 7, 8, 9, 10, 11, 12 or more diffraction peaks in an X-ray powder diffraction pattern using Cu Kα radiation at the following 2θ selected from the group consisting of 6.25±0.20°, 8.06±0.20°, 9.29±0.20°, 11.50±0.20°, 11.95±0.20°, 12.58±0.20°, 14.33±0.20°, 16.15±0.20°, 16.41±0.20°, 18.20±0.20°, 18.75±0.20°, 19.46±0.20°, 20.00±0.20°, 20.57±0.20°, 21.53±0.20°, 21.79±0.20°, 23.11±0.20°, 23.87±0.20°, 24.31±0.20°, 25.26±0.20°, 26.14±0.20°, 26.70±0.20°, 27.71±0.20°, 28.02±0.20°, 28.50±0.20°, 29.09±0.20°, 30.06±0.20°, 30.81±0.20°, 32.39±0.20°, 33.21±0.20° and 33.71±0.20°.

In some embodiments of the present application, the aforementioned crystalline form A of the compound of formula (II) comprises 3, 4, 5, 6, 7, 8, 9, 10, 11, 12 or more diffraction peaks in an X-ray powder diffraction pattern using Cu Kα radiation at the following 2θ selected from the group consisting of 6.25±0.20°, 11.95±0.20°, 12.58±0.20°, 14.33±0.20°, 16.15±0.20°, 19.46±0.20°, 20.00±0.20°, 20.57±0.20°, 21.79±0.20°, 23.87±0.20°, 28.02±0.20° and 30.81±0.20°.

In some embodiments of the present application, the aforementioned crystalline form A of the compound of formula (II) comprises 3, 4, 5, 6, 7 or 8 diffraction peaks in an X-ray powder diffraction pattern using Cu Kα radiation at the following 2θ selected from the group consisting of 6.25±0.20°, 12.58±0.20°, 14.33±0.20°, 16.15±0.20°, 20.00±0.20°, 20.57±0.20°, 21.79±0.20° and 28.02±0.20°.

In some embodiments of the present application, the aforementioned crystalline form A of the compound of formula (II) has an XRPD pattern using Cu Kα radiation as shown in FIG. 1.

In some embodiments of the present application, the aforementioned crystalline form A of the compound of formula (II) has XRPD pattern analysis data using Cu Kα radiation as shown in Table 1.

TABLE 1

XRPD pattern analysis data for crystalline form A of compound of formula (II)

| No. | 2θ (°) | Inter-planar spacing (Å) | Relative intensity (%) |
| --- | --- | --- | --- |
| 1 | 6.25 | 14.15 | 51.54 |
| 2 | 8.06 | 10.97 | 4.42 |
| 3 | 9.29 | 9.52 | 1.53 |
| 4 | 11.50 | 7.69 | 6.83 |
| 5 | 11.95 | 7.40 | 19.50 |
| 6 | 12.58 | 7.04 | 39.24 |
| 7 | 14.33 | 6.18 | 39.55 |
| 8 | 16.15 | 5.49 | 44.87 |
| 9 | 16.41 | 5.40 | 25.16 |
| 10 | 18.20 | 4.88 | 11.79 |
| 11 | 18.75 | 4.73 | 12.07 |
| 12 | 19.46 | 4.56 | 26.74 |
| 13 | 20.00 | 4.44 | 43.30 |
| 14 | 20.57 | 4.32 | 36.44 |
| 15 | 21.53 | 4.13 | 49.75 |
| 16 | 21.79 | 4.08 | 100.00 |
| 17 | 23.11 | 3.85 | 12.56 |
| 18 | 23.87 | 3.73 | 16.00 |
| 19 | 24.31 | 3.66 | 15.05 |
| 20 | 25.26 | 3.53 | 11.31 |
| 21 | 26.14 | 3.41 | 12.82 |
| 22 | 26.70 | 3.34 | 8.25 |

TABLE 1-continued

XRPD pattern analysis data for crystalline form A of compound of formula (II)

| No. | 2θ (°) | Inter-planar spacing (Å) | Relative intensity (%) |
| --- | --- | --- | --- |
| 23 | 27.71 | 3.22 | 20.94 |
| 24 | 28.02 | 3.19 | 27.89 |
| 25 | 28.50 | 3.13 | 13.41 |
| 26 | 29.09 | 3.07 | 9.69 |
| 27 | 30.06 | 2.97 | 12.97 |
| 28 | 30.81 | 2.90 | 18.47 |
| 29 | 32.39 | 2.76 | 5.96 |
| 30 | 33.21 | 2.70 | 10.22 |
| 31 | 33.71 | 2.66 | 6.58 |
| 32 | 34.55 | 2.60 | 6.59 |
| 33 | 36.43 | 2.47 | 3.25 |

In some embodiments of the present application, the aforementioned crystalline form A of the compound of formula (II) has a starting point of an endothermic peak in a differential scanning calorimetry curve at 262.9±5.0° C.

In some embodiments of the present application, the aforementioned crystalline form A of the compound of formula (II) has an endothermic peak in a differential scanning calorimetry curve at 270.0±5.0° C.

In some embodiments of the present application, the aforementioned crystalline form A of the compound of formula (II) has a DSC pattern as shown in FIG. 2.

In some embodiments of the present application, the aforementioned crystalline form A of the compound of formula (II) shows a weight loss of 2.23% in a thermogravimetric analysis curve at 100.0±3.0° C.

In some embodiments of the present application, the aforementioned crystalline form A of the compound of formula (II) has a TGA pattern as shown in FIG. 3.

In another aspect, the present application also provides a method for preparing a crystalline form A of a compound of formula (II), comprising: precipitating the compound of formula (II) from methanol.

In another aspect, the present application also provides a method for preparing the aforementioned crystalline form A of the compound of formula (I), comprising: dissociating the crystalline form A of the compound of formula (II) in a basic aqueous solution; then extracting the crystalline form with an organic solvent, performing concentration under reduced pressure, and adding the crystalline form into the solvent; stirring and filtering to obtain the crystalline form A of the compound of formula (I).

In some embodiments of the present application, the basic aqueous solution is an aqueous sodium carbonate solution, the organic solvent is dichloromethane, and the solvent is methanol.

In another aspect, the present application also provides a method for preparing a crystalline form A of a compound of formula (II), comprising:

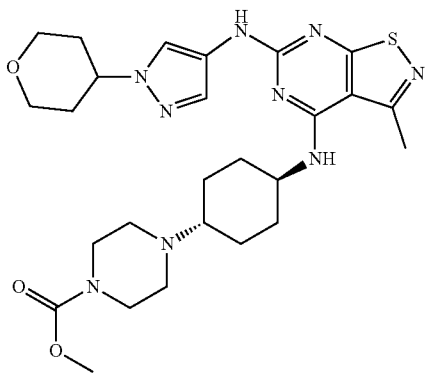

(a) adding a compound of formula (I) into a solvent for dissolving;
(b) adding a hydrochloric acid methanol solution under stirring;
(c) stirring the mixture for 0.5-3 h at 20-30° C.;
(d) filtering and drying the mixture;
wherein the solvent is methanol, and the hydrochloric acid methanol solution has a concentration of 4 mol/L.

In another aspect, the present application also provides a crystalline form of a compound of formula (I),

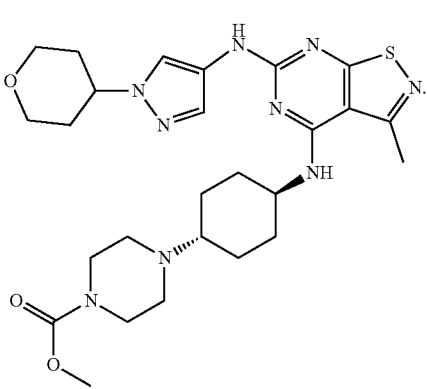

In another aspect, the present application provides a crystalline form A of the compound of formula (I) having characteristic diffraction peaks in an X-ray powder diffraction pattern using Cu Kα radiation at the following 2θ: 16.63±0.20°, 18.54±0.20° and 19.27±0.20°.

In some embodiments of the present application, the aforementioned crystalline form A of the compound of formula (I) has characteristic diffraction peaks in an X-ray powder diffraction pattern using Cu Kα radiation at the following 2θ: 4.40±0.20°, 16.63±0.20°, 18.54±0.20° and 19.27±0.20°.

In some embodiments of the present application, the aforementioned crystalline form A of the compound of formula (I) has characteristic diffraction peaks in an X-ray powder diffraction pattern using Cu Kα radiation at the following 2θ: 4.40±0.20°, 8.75±0.20°, 9.86±0.20°, 16.63±0.20°, 18.54±0.20°, 19.27±0.20°, 19.87±0.20° and 20.85±0.20°.

In some embodiments of the present application, the aforementioned crystalline form A of the compound of formula (I) has characteristic diffraction peaks in an X-ray powder diffraction pattern using Cu Kα radiation at the following 2θ: 4.40±0.20°, 13.11±0.20°, 16.10±0.20°, 16.63±0.20°, 18.54±0.20°, 19.27±0.20°, 19.87±0.20° and 20.85±0.20°.

In some embodiments of the present application, the aforementioned crystalline form A of the compound of formula (I) has characteristic diffraction peaks in an X-ray powder diffraction pattern using Cu Kα radiation at the following 2θ: 4.40±0.20°, 12.31±0.20°, 13.11±0.20°, 13.64±0.20°, 16.10±0.20°, 16.63±0.20°, 18.54±0.20°, 19.27±0.20°, 19.87±0.20°, 20.85±0.20°, 22.18±0.20° and 23.55±0.20°.

In some embodiments of the present application, the aforementioned crystalline form A of the compound of formula (I) has characteristic diffraction peaks in an X-ray powder diffraction pattern using Cu Kα radiation at the following 2θ: 4.40±0.20°, 8.75±0.20°, 9.86±0.20°, 12.31±0.20°, 13.11±0.20°, 13.64±0.20°, 16.10±0.20°, 16.63±0.20°, 18.54±0.20°, 19.27±0.20°, 19.87±0.20°, 20.61±0.20°, 20.85±0.20°, 22.18±0.20° and 23.55±0.20°.

In some embodiments of the present application, the aforementioned crystalline form A of the compound of formula (I) has characteristic diffraction peaks in an X-ray powder diffraction pattern using Cu Kα radiation at the following 2θ: 4.40±0.20°, 8.75±0.20°, 9.86±0.20°, 10.46±0.20°, 11.10±0.20°, 12.31±0.20°, 13.11±0.20°, 13.64±0.20°, 14.01±0.20°, 16.10±0.20°, 16.63±0.20°, 17.05±0.20°, 18.54±0.20°, 19.27±0.20°, 19.87±0.20°, 20.61±0.20°, 20.85±0.20°, 21.95±0.20°, 22.18±0.20°, 23.55±0.20°, 24.73±0.20°, 27.50±0.20°, 28.61±0.20°, 30.05±0.20° and 31.58±0.20°.

The present application provides a crystalline form A of a compound of formula (I) comprising 3, 4, 5, 6, 7, 8, 9, 10, 11, 12 or more diffraction peaks in an X-ray powder diffraction pattern using Cu Kα radiation at the following 2θ selected from the group consisting of 4.40±0.20°, 8.75±0.20°, 9.86±0.20°, 10.46±0.20°, 11.10±0.20°, 12.31±0.20°, 13.11±0.20°, 13.64±0.20°, 14.01±0.20°, 16.10±0.20°, 16.63±0.20°, 17.05±0.20°, 18.54±0.20°, 19.27±0.20°, 19.87±0.20°, 20.61±0.20°, 20.85±0.20°, 21.95±0.20°, 22.18±0.20°, 23.55±0.20°, 24.73±0.20°, 27.50±0.20°, 28.61±0.20°, 30.05±0.20° and 31.58±0.20°.

In some embodiments of the present application, the aforementioned crystalline form A of the compound of formula (I) comprises 3, 4, 5, 6, 7, 8, 9, 10, 11, 12 or more diffraction peaks in an X-ray powder diffraction pattern using Cu Kα radiation at the following 2θ selected from the group consisting of 4.40±0.20°, 12.31±0.20°, 13.11±0.20°, 13.64±0.20°, 16.10±0.20°, 16.63±0.20°, 18.54±0.20°, 19.27±0.20°, 19.87±0.20°, 20.85±0.20°, 22.18±0.20° and 23.55±0.20°.

In some embodiments of the present application, the aforementioned crystalline form A of the compound of formula (I) comprises 3, 4, 5, 6, 7 or 8 diffraction peaks in an X-ray powder diffraction pattern using Cu Kα radiation at the following 2θ selected from the group consisting of 4.40±0.20°, 13.11±0.20°, 16.10±0.20°, 16.63±0.20°, 18.54±0.20°, 19.27±0.20°, 19.87±0.20° and 20.85±0.20°.

In some embodiments of the present application, the aforementioned crystalline form A of the compound of formula (I) has an XRPD pattern using Cu Kα radiation as shown in FIG. 4.

In some embodiments of the present application, the aforementioned crystalline form A of the compound of formula (I) has XRPD pattern analysis data using Cu Kα radiation as shown in Table 2.

TABLE 2

XRPD pattern analysis data for crystalline form A of compound of formula (I)

| No. | 2θ (°) | Interplanar spacing (Å) | Relative intensity (%) |
|---|---|---|---|
| 1 | 4.40 | 20.07 | 14.03 |
| 2 | 8.75 | 10.11 | 7.59 |
| 3 | 9.86 | 8.97 | 4.49 |
| 4 | 10.46 | 8.46 | 4.95 |
| 5 | 11.10 | 7.97 | 6.03 |
| 6 | 12.31 | 7.19 | 12.25 |
| 7 | 13.11 | 6.75 | 16.62 |
| 8 | 13.64 | 6.49 | 10.64 |
| 9 | 14.01 | 6.32 | 6.25 |
| 10 | 16.10 | 5.51 | 12.77 |
| 11 | 16.63 | 5.33 | 37.39 |
| 12 | 17.05 | 5.20 | 7.70 |
| 13 | 18.54 | 4.79 | 33.68 |
| 14 | 19.27 | 4.61 | 100.00 |
| 15 | 19.87 | 4.47 | 29.78 |
| 16 | 20.61 | 4.31 | 18.30 |
| 17 | 20.85 | 4.26 | 25.74 |
| 18 | 21.95 | 4.05 | 7.88 |
| 19 | 22.18 | 4.01 | 11.39 |
| 20 | 23.55 | 3.78 | 10.94 |
| 21 | 24.73 | 3.60 | 4.74 |
| 22 | 27.50 | 3.24 | 6.39 |
| 23 | 28.61 | 3.12 | 4.39 |
| 24 | 30.05 | 2.97 | 6.85 |
| 25 | 31.58 | 2.83 | 0.98 |

In some embodiments of the present application, the aforementioned crystalline form A of the compound of formula (I) has a starting point of an endothermic peak in a differential scanning calorimetry curve at 281.8±5.0° C.

In some embodiments of the present application, the aforementioned crystalline form A of the compound of formula (I) has an endothermic peak in a differential scanning calorimetry curve at 282.6±5.0° C.

In some embodiments of the present application, the aforementioned crystalline form A of the compound of formula (I) has a DSC pattern as shown in FIG. 5.

In some embodiments of the present application, the aforementioned crystalline form A of the compound of formula (I) shows a weight loss of 1.27% in a thermogravimetric analysis curve at 100.0±3.0° C.

In some embodiments of the present application, the aforementioned crystalline form A of the compound of formula (I) has a TGA pattern as shown in FIG. 6.

In another aspect, the present application also provides a compound of formula (III),

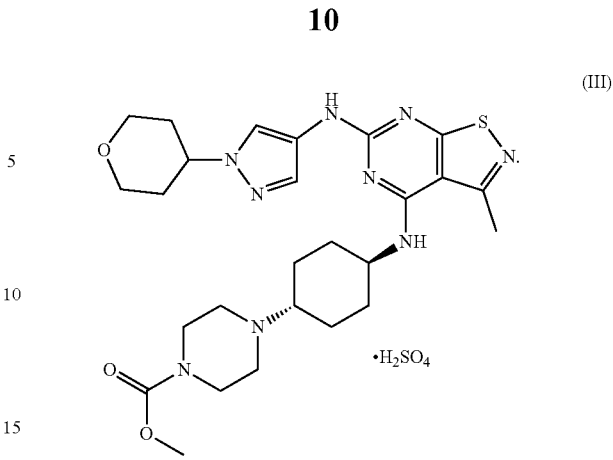

In another aspect, the present application also provides a crystalline form of the compound of formula (III).

In another aspect, the present application provides a crystalline form A of the compound of formula (III) having characteristic diffraction peaks in an X-ray powder diffraction pattern using Cu Kα radiation at the following 2θ: 6.82±0.20°, 7.98±0.20° and 18.02±0.20°.

In some embodiments of the present application, the aforementioned crystalline form A of the compound of formula (III) has characteristic diffraction peaks in an X-ray powder diffraction pattern using Cu Kα radiation at the following 2θ: 6.82±0.20°, 7.98±0.20°, 15.55±0.20°, 18.02±0.20°, 19.34±0.20°, 20.69±0.20°, 22.91±0.20° and 24.08±0.20°.

In some embodiments of the present application, the aforementioned crystalline form A of the compound of formula (III) has characteristic diffraction peaks in an X-ray powder diffraction pattern using Cu Kα radiation at the following 2θ: 6.82±0.20°, 7.98±0.20°, 15.55±0.20°, 18.02±0.20°, 19.34±0.20°, 20.69±0.20°, 22.91±0.20°, 24.08±0.20° and 24.93±0.20°.

In some embodiments of the present application, the aforementioned crystalline form A of the compound of formula (III) has characteristic diffraction peaks in an X-ray powder diffraction pattern using Cu Kα radiation at the following 2θ: 6.82±0.20°, 7.98±0.20°, 15.55±0.20°, 18.02±0.20°, 19.34±0.20°, 20.69±0.20°, 21.33±0.20°, 22.14±0.20°, 22.91±0.20°, 24.08±0.20°, 24.93±0.20° and 26.04±0.20°.

In some embodiments of the present application, the aforementioned crystalline form A of the compound of formula (III) has characteristic diffraction peaks in an X-ray powder diffraction pattern using Cu Kα radiation at the following 2θ: 6.82±0.20°, 7.98±0.20°, 11.61±0.20°, 15.55±0.20°, 17.39±0.20°, 18.02±0.20°, 18.78±0.20°, 19.34±0.20°, 20.26±0.20°, 20.69±0.20°, 21.02±0.20°, 21.33±0.20°, 22.14±0.20°, 22.91±0.20°, 24.08±0.20°, 24.34±0.20°, 24.93±0.20°, 25.18±0.20°, 26.04±0.20° and 27.61±0.20°.

In some embodiments of the present application, the aforementioned crystalline form A of the compound of formula (III) has characteristic diffraction peaks in an X-ray powder diffraction pattern using Cu Kα radiation at the following 2θ: 6.82±0.20°, 7.98±0.20°, 9.02±0.20°, 9.64±0.20°, 11.61±0.20°, 12.13±0.20°, 13.44±0.20°, 15.55±0.20°, 16.61±0.20°, 17.39±0.20°, 18.02±0.20°, 18.78±0.20°, 19.34±0.20°, 20.26±0.20°, 20.69±0.20°, 21.02±0.20°, 21.33±0.20°, 22.14±0.20°, 22.91±0.20°, 24.08±0.20°, 24.34±0.20°, 24.93±0.20°, 25.18±0.20°, 26.04±0.20°, 26.80±0.20°, 27.27±0.20°, 27.61±0.20°, 29.55±0.20° and 31.57±0.20°.

The present application provides a crystalline form A of a compound of formula (III) comprising 3, 4, 5, 6, 7, 8, 9, 10, 11, 12 or more diffraction peaks in an X-ray powder diffraction pattern using Cu Kα radiation at the following 2θ selected from the group consisting of 6.82±0.20°, 7.98±0.20°, 9.02±0.20°, 9.64±0.20°, 11.61±0.20°, 12.13±0.20°, 13.44±0.20°, 15.55±0.20°, 16.61±0.20°, 17.39±0.20°, 18.02±0.20°, 18.78±0.20°, 19.34±0.20°, 20.26±0.20°, 20.69±0.20°, 21.02±0.20°, 21.33±0.20°, 22.14±0.20°, 22.91±0.20°, 24.08±0.20°, 24.34±0.20°, 24.93±0.20°, 25.18±0.20°, 26.04±0.20°, 26.80±0.20°, 27.27±0.20°, 27.61±0.20°, 29.55±0.20° and 31.57±0.20°.

In some embodiments of the present application, the aforementioned crystalline form A of the compound of formula (III) comprises 3, 4, 5, 6, 7, 8, 9, 10, 11, 12 or more diffraction peaks in an X-ray powder diffraction pattern using Cu Kα radiation at the following 2θ selected from the group consisting of 6.82±0.20°, 7.98±0.20°, 15.55±0.20°, 18.02±0.20°, 19.34±0.20°, 20.69±0.20°, 21.33±0.20°, 22.14±0.20°, 22.91±0.20°, 24.08±0.20°, 24.93±0.20° and 26.04±0.20°.

In some embodiments of the present application, the aforementioned crystalline form A of the compound of formula (III) comprises 3, 4, 5, 6, 7 or 8 diffraction peaks in an X-ray powder diffraction pattern using Cu Kα radiation at the following 2θ selected from the group consisting of 6.82±0.20°, 7.98±0.20°, 15.55±0.20°, 18.02±0.20°, 19.34±0.20°, 20.69±0.20°, 22.91±0.20° and 24.08±0.20°.

In some embodiments of the present application, the aforementioned crystalline form A of the compound of formula (III) has an XRPD pattern using Cu Kα radiation as shown in FIG. 7.

In some embodiments of the present application, the aforementioned crystalline form A of the compound of formula (III) has XRPD pattern analysis data using Cu Kα radiation as shown in Table 3.

TABLE 3

XRPD pattern analysis data for crystalline form A of compound of formula (III)

| No. | 2θ (°) | Interplanar spacing (Å) | Relative intensity (%) |
| --- | --- | --- | --- |
| 1 | 6.82 | 12.96 | 47.61 |
| 2 | 7.98 | 11.09 | 58.40 |
| 3 | 9.02 | 9.81 | 8.30 |
| 4 | 9.64 | 9.18 | 2.90 |
| 5 | 11.66 | 7.59 | 12.07 |
| 6 | 12.13 | 7.30 | 9.57 |
| 7 | 13.44 | 6.59 | 8.67 |
| 8 | 15.55 | 5.70 | 23.09 |
| 9 | 16.61 | 5.34 | 7.08 |
| 10 | 17.39 | 5.10 | 11.74 |
| 11 | 18.02 | 4.92 | 100.00 |
| 12 | 18.78 | 4.73 | 12.83 |
| 13 | 19.34 | 4.59 | 28.08 |
| 14 | 20.26 | 4.38 | 19.11 |
| 15 | 20.69 | 4.29 | 22.40 |
| 16 | 21.02 | 4.23 | 19.47 |
| 17 | 21.33 | 4.17 | 15.52 |
| 18 | 22.14 | 4.02 | 13.74 |
| 19 | 22.91 | 3.88 | 20.87 |
| 20 | 24.08 | 3.70 | 28.29 |
| 21 | 24.34 | 3.66 | 15.70 |
| 22 | 24.93 | 3.57 | 20.15 |

TABLE 3-continued

XRPD pattern analysis data for crystalline form A of compound of formula (III)

| No. | 2θ (°) | Interplanar spacing (Å) | Relative intensity (%) |
| --- | --- | --- | --- |
| 23 | 25.18 | 3.54 | 19.19 |
| 24 | 26.04 | 3.42 | 16.01 |
| 25 | 26.80 | 3.33 | 6.37 |
| 26 | 27.27 | 3.27 | 7.77 |
| 27 | 27.61 | 3.23 | 12.88 |
| 28 | 29.55 | 3.02 | 5.09 |
| 29 | 31.57 | 2.83 | 2.82 |

In some embodiments of the present application, the aforementioned crystalline form A of the compound of formula (III) has an endothermic peak in a differential scanning calorimetry curve at 88.0±3.0° C. and a starting point of the endothermic peak in a differential scanning calorimetry curve at 176.3±5.0° C.

In some embodiments of the present application, the aforementioned crystalline form A of the compound of formula (III) has a DSC pattern as shown in FIG. 8.

In some embodiments of the present application, the aforementioned crystalline form A of the compound of formula (III) shows a weight loss of 4.45% in a thermogravimetric analysis curve at 100.0±3.0° C.

In some embodiments of the present application, the aforementioned crystalline form A of the compound of formula (III) has a TGA pattern as shown in FIG. 9.

In another aspect, the present application also provides a compound of formula (IV),

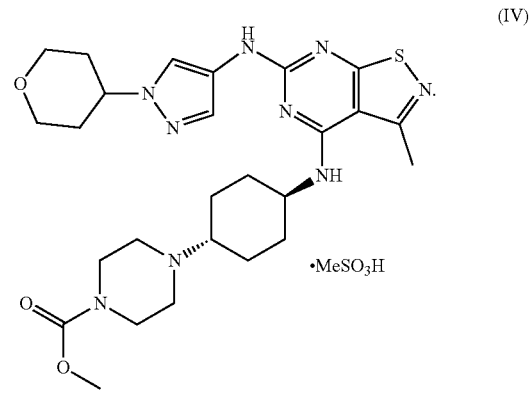 [SMILES: "·MeSO3H" ; COC(=O)N1CCN([C@H]2CC[C@H](Nc3nc(Nc4cnn(C5CCOCC5)c4)nc4snc(C)c34)CC2)CC1]

(IV)

In another aspect, the present application also provides a crystalline form of a compound of formula (IV).

In another aspect, the present application provides a crystalline form A of the compound of formula (IV) having characteristic diffraction peaks in an X-ray powder diffraction pattern using Cu Kα radiation at the following 2θ: 6.78±0.20°, 18.09±0.20° and 21.72±0.20°.

In some embodiments of the present application, the aforementioned crystalline form A of the compound of formula (IV) has characteristic diffraction peaks in an X-ray powder diffraction pattern using Cu Kα radiation at the following 2θ: 6.78±0.20°, 13.52±0.20°, 18.09±0.20° and 21.72±0.20°.

In some embodiments of the present application, the aforementioned crystalline form A of the compound of formula (IV) has characteristic diffraction peaks in an X-ray powder diffraction pattern using Cu Kα radiation at the following 2θ: 6.78±0.20°, 7.24±0.20°, 7.87±0.20°, 13.52±0.20°, 18.09±0.20°, 19.65±0.20°, 21.01±0.20° and 21.72±0.20°.

In some embodiments of the present application, the aforementioned crystalline form A of the compound of formula (IV) has characteristic diffraction peaks in an X-ray powder diffraction pattern using Cu Kα radiation at the following 2θ: 6.78±0.20°, 13.52±0.20°, 18.09±0.20°, 19.65±0.20°, 21.01±0.20°, 21.72±0.20°, 23.22±0.20° and 23.60±0.20°.

In some embodiments of the present application, the aforementioned crystalline form A of the compound of formula (IV) has characteristic diffraction peaks in an X-ray powder diffraction pattern using Cu Kα radiation at the following 2θ: 6.78±0.20°, 7.24±0.20°, 7.87±0.20°, 13.52±0.20°, 18.09±0.20°, 19.25±0.20°, 19.65±0.20°, 20.30±0.20°, 21.01±0.20°, 21.72±0.20°, 23.22±0.20° and 23.60±0.20°.

In some embodiments of the present application, the aforementioned crystalline form A of the compound of formula (IV) has characteristic diffraction peaks in an X-ray powder diffraction pattern using Cu Kα radiation at the following 2θ: 6.78±0.20°, 7.87±0.20°, 13.52±0.20°, 16.69±0.20°, 18.09±0.20°, 19.65±0.20°, 20.30±0.20°, 21.01±0.20°, 21.72±0.20°, 23.22±0.20°, 23.60±0.20° and 27.04±0.20°.

In some embodiments of the present application, the aforementioned crystalline form A of the compound of formula (IV) has characteristic diffraction peaks in an X-ray powder diffraction pattern using Cu Kα radiation at the following 2θ: 6.78±0.20°, 7.24±0.20°, 7.87±0.20°, 12.06±0.20°, 12.74±0.20°, 12.96±0.20°, 13.52±0.20°, 18.09±0.20°, 18.87±0.20°, 19.25±0.20°, 19.65±0.20°, 20.30±0.20°, 21.01±0.20°, 21.72±0.20°, 22.86±0.20°, 23.22±0.20°, 23.60±0.20°, 25.09±0.20°, 25.42±0.20°, 25.59±0.20°, 26.04±0.20°, 27.04±0.20°, 27.80±0.20°, 28.82±0.20°, 30.06±0.20°, 30.72±0.20°, 31.32±0.20°, 32.57±0.20°, 33.13±0.20°, 34.59±0.20°, 36.00±0.20° and 37.63±0.20°.

The present application provides a crystalline form A of a compound of formula (IV) comprising 3, 4, 5, 6, 7, 8, 9, 10, 11, 12 or more peaks in an X-ray powder diffraction pattern using Cu Kα radiation at the following 2θ selected from the group consisting of 6.78±0.20°, 7.24±0.20°, 7.87±0.20°, 12.06±0.20°, 12.74±0.20°, 12.96±0.20°, 13.52±0.20°, 18.09±0.20°, 18.87±0.20°, 19.25±0.20°, 19.65±0.20°, 20.30±0.20°, 21.01±0.20°, 21.72±0.20°, 22.86±0.20°, 23.22±0.20°, 23.60±0.20°, 25.09±0.20°, 25.42±0.20°, 25.59±0.20°, 26.04±0.20°, 27.04±0.20°, 27.80±0.20°, 28.82±0.20°, 30.06±0.20°, 30.72±0.20°, 31.32±0.20°, 32.57±0.20°, 33.13±0.20°, 34.59±0.20°, 36.00±0.20° and 37.63±0.20°.

In some embodiments of the present application, the aforementioned crystalline form A of the compound of formula (IV) comprises 3, 4, 5, 6, 7, 8, 9, 10, 11, 12 or more diffraction peaks in an X-ray powder diffraction pattern using Cu Kα radiation at the following 2θ selected from the group consisting of 6.78±0.20°, 7.87±0.20°, 13.52±0.20°, 16.69±0.20°, 18.09±0.20°, 19.65±0.20°, 20.30±0.20°, 21.01±0.20°, 21.72±0.20°, 23.22±0.20°, 23.60±0.20° and 27.04±0.20°.

In some embodiments of the present application, the aforementioned crystalline form A of the compound of formula (IV) comprises 3, 4, 5, 6, 7 or 8 diffraction peaks in an X-ray powder diffraction pattern using Cu K radiation at the following 2θ selected from the group consisting of 6.78±0.20°, 13.52±0.20°, 18.090.20°, 19.657±0.20°, 21.01±0.20°, 21.72±0.20°, 23.22±0.20° and 23.60±0.20°.

In some embodiments of the present application, the aforementioned crystalline form A of the compound of formula (IV) has an XRPD pattern using Cu Kα radiation as shown in FIG. 10.

In some embodiments of the present application, the aforementioned crystalline form A of the compound of formula (IV) has XRPD pattern analysis data using Cu Kα radiation as shown in Table 4.

TABLE 4

XRPD pattern analysis data for crystalline form A of compound of formula (IV)

| No. | 2θ (°) | Inter-planar spacing (Å) | Relative intensity (%) |
|---|---|---|---|
| 1 | 6.78 | 13.04 | 25.55 |
| 2 | 7.24 | 12.21 | 4.41 |
| 3 | 7.87 | 11.23 | 8.51 |
| 4 | 12.06 | 7.34 | 4.93 |
| 5 | 12.74 | 6.95 | 3.67 |
| 6 | 12.96 | 6.83 | 3.20 |
| 7 | 13.52 | 6.55 | 23.55 |
| 8 | 15.72 | 5.64 | 1.97 |
| 9 | 16.69 | 5.31 | 9.73 |
| 10 | 18.09 | 4.90 | 100.00 |
| 11 | 18.87 | 4.70 | 4.43 |
| 12 | 19.25 | 4.61 | 14.46 |
| 13 | 19.65 | 4.52 | 25.13 |
| 14 | 20.30 | 4.37 | 11.57 |
| 15 | 21.01 | 4.23 | 22.57 |
| 16 | 21.72 | 4.09 | 34.65 |
| 17 | 22.86 | 3.89 | 5.84 |
| 18 | 23.22 | 3.83 | 11.78 |
| 19 | 23.60 | 3.77 | 14.09 |
| 20 | 25.09 | 3.55 | 2.77 |
| 21 | 25.42 | 3.50 | 6.68 |
| 22 | 25.59 | 3.48 | 6.21 |
| 23 | 26.04 | 3.42 | 2.72 |
| 24 | 27.04 | 3.30 | 6.79 |
| 25 | 27.80 | 3.21 | 4.85 |
| 26 | 28.82 | 3.10 | 4.13 |
| 27 | 30.06 | 2.97 | 4.49 |
| 28 | 30.72 | 2.91 | 1.74 |
| 29 | 31.32 | 2.86 | 2.04 |
| 30 | 32.57 | 2.75 | 2.06 |
| 31 | 33.13 | 2.70 | 2.42 |
| 32 | 34.95 | 2.57 | 2.31 |
| 33 | 36.00 | 2.49 | 1.17 |
| 34 | 37.63 | 2.39 | 0.66 |

In some embodiments of the present application, the aforementioned crystalline form A of the compound of formula (IV) has a starting point of an endothermic peak in a differential scanning calorimetry curve at 247.4±5.0° C.

In some embodiments of the present application, the aforementioned crystalline form A of the compound of formula (IV) has an endothermic peak in a differential scanning calorimetry curve at 249.8±5.0° C.

In some embodiments of the present application, the aforementioned crystalline form A of the compound of formula (IV) has a DSC pattern as shown in FIG. 11.

In some embodiments of the present application, the aforementioned crystalline form A of the compound of formula (IV) shows a weight loss of 3.11% in a thermogravimetric analysis curve at 120.0±3.0° C.

In some embodiments of the present application, the aforementioned crystalline form A of the compound of formula (IV) has a TGA pattern as shown in FIG. 12.

In another aspect, the present application also provides a compound of formula (V),

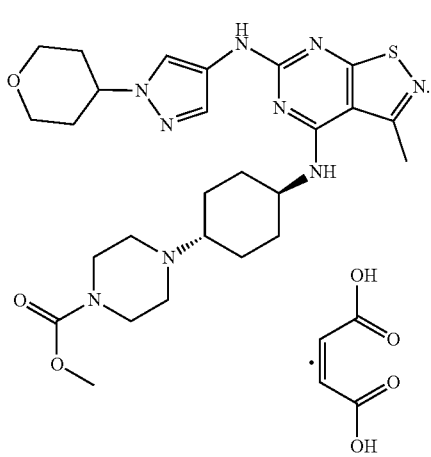

In another aspect, the present application also provides a crystalline form of a compound of formula (V).

In another aspect, the present application provides a crystalline form A of the compound of formula (V) having characteristic diffraction peaks in an X-ray powder diffraction pattern using Cu Kα radiation at the following 2θ: 17.72±0.20°, 19.73±0.20° and 22.32±0.20°.

The present application provides a crystalline form A of the compound of formula (V) having characteristic diffraction peaks in an X-ray powder diffraction pattern using Cu Kα radiation at the following 2θ: 17.72±0.20°, 19.50±0.20° and 22.32±0.20°.

The present application provides a crystalline form A of the compound of formula (V) having characteristic diffraction peaks in an X-ray powder diffraction pattern using Cu Kα radiation at the following 2θ: 19.50±0.20°, 19.73±0.20° and 22.32±0.20°.

In some embodiments of the present application, the aforementioned crystalline form A of the compound of formula (V) has characteristic diffraction peaks in an X-ray powder diffraction pattern using Cu Kα radiation at the following 2θ: 17.72±0.20°, 19.50±0.20°, 19.73±0.20°, 21.32±0.20° and 22.32±0.20°.

In some embodiments of the present application, the aforementioned crystalline form A of the compound of formula (V) has characteristic diffraction peaks in an X-ray powder diffraction pattern using Cu Kα radiation at the following 2θ: 17.72±0.20°, 19.50±0.20°, 19.73±0.20°, 21.05±0.20° and 22.32±0.20°.

In some embodiments of the present application, the aforementioned crystalline form A of the compound of formula (V) has characteristic diffraction peaks in an X-ray powder diffraction pattern using Cu Kα radiation at the following 2θ: 17.72±0.20°, 19.73±0.20°, 21.05±0.20°, 21.32±0.20° and 22.32±0.20°.

In some embodiments of the present application, the aforementioned crystalline form A of the compound of formula (V) has characteristic diffraction peaks in an X-ray powder diffraction pattern using Cu Kα radiation at the following 2θ: 17.72±0.20°, 19.50±0.20°, 21.05±0.20°, 21.32±0.20° and 22.32±0.20°.

In some embodiments of the present application, the aforementioned crystalline form A of the compound of formula (V) has characteristic diffraction peaks in an X-ray powder diffraction pattern using Cu Kα radiation at the following 2θ: 17.72±0.20°, 19.50±0.20°, 19.73±0.20°, 21.05±0.20°, 21.32±0.20° and 22.32±0.20°.

In some embodiments of the present application, the aforementioned crystalline form A of the compound of formula (V) has characteristic diffraction peaks in an X-ray powder diffraction pattern using Cu Kα radiation at the following 2θ: 16.67±0.20°, 17.72±0.20°, 18.17±0.20°, 19.73±0.20°, 21.05±0.20°, 22.32±0.20°, 23.45±0.20° and 24.89±0.20°.

In some embodiments of the present application, the aforementioned crystalline form A of the compound of formula (V) has characteristic diffraction peaks in an X-ray powder diffraction pattern using Cu Kα radiation at the following 2θ: 12.54±0.20°, 13.04±0.20°, 15.96±0.20°, 16.67±0.20°, 17.72±0.20°, 18.17±0.20°, 19.73±0.20°, 21.05±0.20°, 22.32±0.20°, 23.45±0.20°, 24.89±0.20° and 25.61±0.20°.

In some embodiments of the present application, the aforementioned crystalline form A of the compound of formula (V) has characteristic diffraction peaks in an X-ray powder diffraction pattern using Cu Kα radiation at the following 2θ: 4.23±0.20°, 8.37±0.20°, 10.02±0.20°, 12.54±0.20°, 13.04±0.20°, 13.73±0.20°, 15.96±0.20°, 16.67±0.20°, 17.72±0.20°, 18.17±0.20°, 19.50±0.20°, 19.73±0.20°, 21.05±0.20°, 21.32±0.20°, 22.32±0.20°, 23.45±0.20°, 24.89±0.20°, 25.61±0.20° and 26.80±0.20°.

In some embodiments of the present application, the aforementioned crystalline form A of the compound of formula (V) has characteristic diffraction peaks in an X-ray powder diffraction pattern using Cu Kα radiation at the following 2θ: 4.23±0.20°, 8.37±0.20°, 10.02±0.20°, 10.90±0.20°, 11.85±0.20°, 12.54±0.20°, 13.04±0.20°, 13.73±0.20°, 14.48±0.20°, 15.05±0.20°, 15.96±0.20°, 16.67±0.20°, 17.72±0.20°, 18.17±0.20°, 19.50±0.20°, 19.73±0.20°, 21.05±0.20°, 21.32±0.20°, 22.32±0.20°, 23.45±0.20°, 24.89±0.20°, 25.61±0.20°, 26.80±0.20°, 27.32±0.20°, 30.42±0.20° and 33.09±0.20°.

The present application provides a crystalline form A of a compound of formula (V) comprising 3, 4, 5, 6, 7, 8, 9, 10, 11, 12 or more diffraction peaks in an X-ray powder diffraction pattern using Cu Kα radiation at the following 2θ selected from the group consisting of 4.23±0.20°, 8.37±0.20°, 10.02±0.20°, 10.90±0.20°, 11.85±0.20°, 12.54±0.20°, 13.04±0.20°, 13.73±0.20°, 14.48±0.20°, 15.05±0.20°, 15.96±0.20°, 16.67±0.20°, 17.72±0.20°, 18.17±0.20°, 19.50±0.20°, 19.73±0.20°, 21.05±0.20°, 21.32±0.20°, 22.32±0.20°, 23.45±0.20°, 24.89±0.20°, 25.61±0.20°, 26.80±0.20°, 27.32±0.20°, 30.42±0.20° and 33.09±0.20°.

In some embodiments of the present application, the aforementioned crystalline form A of the compound of formula (V) comprises 3, 4, 5, 6, 7, 8, 9, 10, 11, 12 or more diffraction peaks in an X-ray powder diffraction pattern using Cu K radiation at the following 2θ selected from the group consisting of 12.54±0.20°, 13.04±0.20°, 15.967±0.20°, 16.67±0.20°, 17.72±0.20°, 18.17±0.20°, 19.73±0.20°, 21.05±0.20°, 22.3250.20°, 23.45±0.20°, 24.895±0.20° and 25.61±0.20°.

In some embodiments of the present application, the aforementioned crystalline form A of the compound of formula (V) comprises 3, 4, 5, 6, 7 or 8 diffraction peaks in an X-ray powder diffraction pattern using Cu Kα radiation at the following 2θ selected from the group consisting of 16.67±0.20°, 17.72±0.20°, 18.17±0.20°, 19.730.20°, 21.05±0.206, 22.3±20.20°, 23.45±0.20 and 24.892±0.20°.

In some embodiments of the present application, the aforementioned crystalline form A of the compound of formula (V) has an XRPD pattern using Cu Kα radiation as shown in FIG. 13.

In some embodiments of the present application, the aforementioned crystalline form A of the compound of formula (V) has XRPD pattern analysis data using Cu Kα radiation as shown in Table 5.

TABLE 5

XRPD pattern analysis data for crystalline form A of compound of formula (V)

| No. | 2θ (°) | Inter-planar spacing (Å) | Relative intensity (%) |
|---|---|---|---|
| 1 | 4.23 | 20.89 | 10.14 |
| 2 | 8.37 | 10.57 | 10.86 |
| 3 | 10.02 | 8.83 | 12.31 |
| 4 | 10.90 | 8.12 | 5.43 |
| 5 | 11.85 | 7.47 | 7.44 |
| 6 | 12.54 | 7.06 | 13.00 |
| 7 | 13.04 | 6.79 | 15.83 |
| 8 | 13.73 | 6.45 | 11.46 |
| 9 | 14.48 | 6.12 | 9.81 |
| 10 | 15.05 | 5.89 | 6.93 |
| 11 | 15.96 | 5.55 | 13.47 |
| 12 | 16.67 | 5.32 | 21.13 |
| 13 | 17.72 | 5.01 | 46.46 |
| 14 | 18.17 | 4.88 | 18.71 |
| 15 | 19.50 | 4.55 | 95.22 |
| 16 | 19.73 | 4.50 | 100.00 |
| 17 | 21.05 | 4.22 | 37.83 |
| 18 | 21.32 | 4.17 | 34.12 |
| 19 | 22.32 | 3.98 | 52.54 |
| 20 | 23.45 | 3.79 | 23.59 |
| 21 | 24.89 | 3.58 | 20.52 |
| 22 | 25.61 | 3.48 | 12.79 |
| 23 | 26.80 | 3.33 | 11.01 |
| 24 | 27.32 | 3.26 | 3.40 |
| 25 | 30.42 | 2.94 | 7.61 |
| 26 | 33.09 | 2.71 | 3.98 |

In some embodiments of the present application, the aforementioned crystalline form A of the compound of formula (V) has starting points of endothermic peaks in a differential scanning calorimetry curve at 182.2±5.0° C. and 194.2±5.0° C.

In some embodiments of the present application, the aforementioned crystalline form A of the compound of formula (V) has endothermic peaks in a differential scanning calorimetry curve at 185.9±5.0° C. and 199.5±5.0° C.

In some embodiments of the present application, the aforementioned crystalline form A of the compound of formula (V) has a DSC pattern as shown in FIG. 14.

In some embodiments of the present application, the aforementioned crystalline form A of the compound of formula (V) shows a weight loss of 3.62% in a thermogravimetric analysis curve at 100.0±3.0° C.

In some embodiments of the present application, the aforementioned crystalline form A of the compound of formula (V) has a TGA pattern as shown in FIG. 15.

In another aspect, the present application also provides a compound of formula (VI),

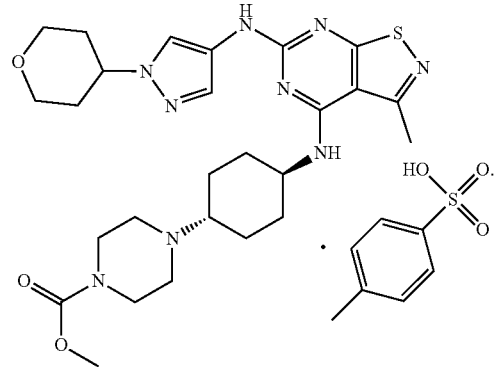

(VI)

In another aspect, the present application also provides a crystalline form of a compound of formula (VI).

In another aspect, the present application provides a crystalline form A of the compound of formula (VI) having characteristic diffraction peaks in an X-ray powder diffraction pattern using Cu Kα radiation at the following 2θ: 7.66±0.20°, 20.15±0.20° and 23.34±0.20°.

The present application also provides a crystalline form A of the compound of formula (VI) having characteristic diffraction peaks in an X-ray powder diffraction pattern using Cu Kα radiation at the following 2θ: 20.15±0.20°, 23.34±0.20° and 24.77±0.20°.

In some embodiments of the present application, the aforementioned crystalline form A of the compound of formula (VI) has characteristic diffraction peaks in an X-ray powder diffraction pattern using Cu Kα radiation at the following 2θ: 7.66±0.20°, 20.15±0.20°, 23.34±0.20° and 24.77±0.20°.

In some embodiments of the present application, the aforementioned crystalline form A of the compound of formula (VI) has characteristic diffraction peaks in an X-ray powder diffraction pattern using Cu Kα radiation at the following 2θ: 7.66±0.20°, 12.15±0.20°, 16.56±0.20°, 18.90±0.20°, 20.15±0.20°, 22.02±0.20°, 23.34±0.20° and 24.77±0.20°.

In some embodiments of the present application, the aforementioned crystalline form A of the compound of formula (VI) has characteristic diffraction peaks in an X-ray powder diffraction pattern using Cu Kα radiation at the following 2θ: 7.66±0.20°, 12.15±0.20°, 16.56±0.20°, 18.90±0.20°, 20.15±0.20°, 21.73±0.20°, 23.34±0.20° and 24.77±0.20°.

In some embodiments of the present application, the aforementioned crystalline form A of the compound of formula (VI) has characteristic diffraction peaks in an X-ray powder diffraction pattern using Cu Kα radiation at the following 2θ: 7.66±0.20°, 12.15±0.20°, 16.56±0.20°, 18.90±0.20°, 20.15±0.20°, 21.73±0.20°, 22.02±0.20°, 23.34±0.20° and 24.77±0.20°.

In some embodiments of the present application, the aforementioned crystalline form A of the compound of formula (VI) has characteristic diffraction peaks in an X-ray powder diffraction pattern using Cu Kα radiation at the following 2θ: 7.66±0.20°, 12.15±0.20°, 16.13±0.20°, 16.56±0.20°, 17.08±0.20°, 17.62±0.20°, 18.90±0.20°, 20.15±0.20°, 22.02±0.20°, 23.34±0.20°, 24.77±0.20° and 30.00±0.20°.

In some embodiments of the present application, the aforementioned crystalline form A of the compound of formula (VI) has characteristic diffraction peaks in an X-ray powder diffraction pattern using Cu Kα radiation at the following 2θ: 7.66±0.20°, 8.23±0.20°, 12.15±0.20°, 16.13±0.20°, 16.56±0.20°, 17.08±0.20°, 17.62±0.20°, 18.90±0.20°, 20.15±0.20°, 21.73±0.20°, 22.02±0.20°, 23.34±0.20°, 24.77±0.20° and 30.00±0.20°.

In some embodiments of the present application, the aforementioned crystalline form A of the compound of formula (VI) has characteristic diffraction peaks in an X-ray powder diffraction pattern using Cu Kα radiation at the following 2θ: 6.05°, 7.66°, 8.23°, 12.15°, 13.16°, 13.78°, 14.20°, 14.73°, 15.35°, 16.13°, 16.56°, 17.08°, 17.620, 18.02°, 18.90°, 20.15°, 20.90°, 21.73°, 22.02°, 23.34°, 24.77°, 26.47°, 27.50°, 28.43°, 29.29° and 30.00°.

In some embodiments of the present application, the aforementioned crystalline form A of the compound of formula (VI) has characteristic diffraction peaks in an X-ray powder diffraction pattern using Cu Kα radiation at the following 2θ: 6.05±0.20°, 7.66±0.20°, 8.23±0.20°, 12.15±0.20°, 13.16±0.20°, 13.78±0.20°, 14.20±0.20°, 14.73±0.20°, 15.35±0.20°, 16.13±0.20°, 16.56±0.20°, 17.08±0.20°, 17.62±0.20°, 18.02±0.20°, 18.90±0.20°, 20.15±0.20°, 20.90±0.20°, 21.73±0.20°, 22.02±0.20°, 23.34±0.20°, 24.77±0.20°, 26.47±0.20°, 27.50±0.20°, 28.43±0.20°, 29.29±0.20°, 30.00±0.20°, 30.86±0.20°, 32.62±0.20°, 36.10±0.20°, 37.01±0.20° and 38.49±0.20°.

The present application provides a crystalline form A of a compound of formula (VI) comprising 3, 4, 5, 6, 7, 8, 9, 10, 11, 12 or more diffraction peaks in an X-ray powder diffraction pattern using Cu Kα radiation at the following 2θ selected from the group consisting of 6.05±0.20°, 7.66±0.20°, 8.23±0.20°, 12.15±0.20°, 13.16±0.20°, 13.78±0.20°, 14.20±0.20°, 14.73±0.20°, 15.35±0.20°, 16.13±0.20°, 16.56±0.20°, 17.08±0.20°, 17.62±0.20°, 18.02±0.20°, 18.90±0.20°, 20.15±0.20°, 20.90±0.20°, 21.73±0.20°, 22.02±0.20°, 23.34±0.20°, 24.77±0.20°, 26.47±0.20°, 27.50±0.20°, 28.43±0.20°, 29.29±0.20°, 30.00±0.20°, 30.86±0.20°, 32.62±0.20°, 36.10±0.20°, 37.01±0.20° and 38.49±0.20°.

In some embodiments of the present application, the aforementioned crystalline form A of the compound of formula (VI) comprises 3, 4, 5, 6, 7, 8, 9, 10, 11, 12 or more diffraction peaks in an X-ray powder diffraction pattern using Cu K radiation at the following 2θ selected from the group consisting of 7.66±0.20°, 12.15±0.209, 16.13±0.20°, 16.56±0.20°, 17.08±0.20°, 17.62±0.20, 18.90±0.2°, 20.15±0.20°, 22.02±0.20°, 23.34±0.20°, 24.77±0.20° and 30.00±0.20°.

In some embodiments of the present application, the aforementioned crystalline form A of the compound of formula (VI) comprises 3, 4, 5, 6, 7 or 8 diffraction peaks in an X-ray powder diffraction pattern using Cu Kα radiation at the following 2θ selected from the group consisting of 7.663±0.20°, 12.15±0.20°, 16.56±0.20°, 18.90±0.20°, 20.15±0.20°, 22.02±0.20°, 23.34±0.20° and 24.77±0.20°.

In some embodiments of the present application, the aforementioned crystalline form A of the compound of formula (VI) has an XRPD pattern using Cu Kα radiation as shown in FIG. 16.

In some embodiments of the present application, the aforementioned crystalline form A of the compound of formula (VI) has XRPD pattern analysis data using Cu Kα radiation as shown in Table 6.

TABLE 6

XRPD pattern analysis data for crystalline form A of compound of formula (VI)

| No. | 2θ (°) | Inter-planar spacing (Å) | Relative intensity (%) |
|---|---|---|---|
| 1 | 6.05 | 14.61 | 1.89 |
| 2 | 7.66 | 11.55 | 33.26 |
| 3 | 8.23 | 10.74 | 5.34 |
| 4 | 12.15 | 7.29 | 21.38 |
| 5 | 13.16 | 6.73 | 3.07 |
| 6 | 13.78 | 6.43 | 1.96 |
| 7 | 14.20 | 6.24 | 2.33 |
| 8 | 14.73 | 6.02 | 3.20 |
| 9 | 15.35 | 5.77 | 6.71 |
| 10 | 16.13 | 5.49 | 17.02 |
| 11 | 16.56 | 5.35 | 31.17 |
| 12 | 17.08 | 5.19 | 15.63 |
| 13 | 17.62 | 5.03 | 18.16 |
| 14 | 18.02 | 4.92 | 6.21 |
| 15 | 18.90 | 4.69 | 21.94 |
| 16 | 20.15 | 4.41 | 68.26 |
| 17 | 20.90 | 4.25 | 6.22 |
| 18 | 21.73 | 4.09 | 26.17 |
| 19 | 22.02 | 4.04 | 27.29 |
| 20 | 23.34 | 3.81 | 100.00 |
| 21 | 24.77 | 3.59 | 39.32 |
| 22 | 26.47 | 3.37 | 4.31 |
| 23 | 27.50 | 3.24 | 2.53 |
| 24 | 28.43 | 3.14 | 1.63 |
| 25 | 29.29 | 3.05 | 7.09 |
| 26 | 30.00 | 2.98 | 9.57 |
| 27 | 30.86 | 2.90 | 1.70 |
| 28 | 32.62 | 2.74 | 6.01 |
| 29 | 36.10 | 2.49 | 1.99 |
| 30 | 37.01 | 2.43 | 2.94 |
| 31 | 38.49 | 2.34 | 2.24 |

In some embodiments of the present application, the aforementioned crystalline form A of the compound of formula (VI) has a starting point of an endothermic peak in a differential scanning calorimetry curve at 262.9±5.0° C.

In some embodiments of the present application, the aforementioned crystalline form A of the compound of formula (VI) has an endothermic peak in a differential scanning calorimetry curve at 264.2±5.0° C.

In some embodiments of the present application, the aforementioned crystalline form A of the compound of formula (VI) has a DSC pattern as shown in FIG. 17.

In some embodiments of the present application, the aforementioned crystalline form A of the compound of formula (VI) shows a weight loss of 2.17% in a thermogravimetric analysis curve at 250.0±3.0° C.

In some embodiments of the present application, the aforementioned crystalline form A of the compound of formula (VI) has a TGA pattern as shown in FIG. 18.

The present application also provides a method for preparing the aforementioned crystalline form A of the compound of formula (III), the aforementioned crystalline form A of the compound of formula (IV), the aforementioned crystalline form A of the compound of formula (V), and the aforementioned crystalline form A of the compound of formula (VI), comprising: adding the crystalline form A of the compound of formula (I) into a solvent; then adding an acid, heating and stirring the mixture, and cooling and filtering the mixture to obtain crystalline forms.

In some embodiments of the present application, the solvent is methanol; the heating is performed at a temperature of 40° C. to 60° C., preferably 50° C.

In another aspect, the present application provides a crystalline composition comprising the crystalline form A of the compound of formula (I), the crystalline form A of the compound of formula (II), the crystalline form A of the compound of formula (III), the crystalline form A of the compound of formula (IV), the crystalline form A of the compound of formula (V), or the crystalline form A of the compound of formula (VI), wherein the crystalline form A of the compound of formula (I), the crystalline form A of the compound of formula (II), the crystalline form A of the compound of formula (III), the crystalline form A of the compound of formula (IV), the crystalline form A of the compound of formula (V), or the crystalline form A of the compound of formula (VI) accounts for 50% or more, preferably 75% or more, more preferably 90% or more, and most preferably 95% or more of the weight of the crystalline composition. The crystalline compositions may also comprise small amounts of other crystalline forms or amorphous forms of the compound of formula (I), the compound of formula (II), the compound of formula (III), the compound of formula (IV), the compound of formula (V), or the compound of formula (VI).

In another aspect, the present application provides a pharmaceutical composition comprising a therapeutically effective amount of the compound of formula (I), the compound of formula (II), the compound of formula (III), the compound of formula (IV), the compound of formula (V) or the compound of formula (VI) described above, or a crystalline form thereof, or a crystalline composition of the crystalline form thereof; the pharmaceutical composition may comprise at least one pharmaceutically acceptable carrier or other excipients. In addition, the pharmaceutical composition disclosed herein may further comprise one or more additional therapeutic agents.

In another aspect, the present application provides use of the compound of formula (I), the compound of formula (II), the compound of formula (III), the compound of formula (IV), the compound of formula (V) or the compound of formula (VI) or the crystalline form thereof described above, or the aforementioned crystalline composition, or the aforementioned pharmaceutical composition in preparing a medicament for the treatment or prevention of an IRAK4-related disease.

In another aspect, the present application provides the compound of formula (I), the compound of formula (II), the compound of formula (III), the compound of formula (IV), the compound of formula (V) or the compound of formula (VI) or the crystalline form thereof described above, or the aforementioned crystalline composition, or the aforementioned pharmaceutical composition for use in a medicament for treating or preventing an IRAK4-related disease.

In another aspect, the present application provides a method for treating or preventing an IRAK4-related disease, comprising administering to a mammal in need thereof a therapeutically effective amount of the compound of formula (I), the compound of formula (II), the compound of formula (III), the compound of formula (IV), the compound of formula (V) or the compound of formula (VI) or the crystalline form thereof described above, or the aforementioned crystalline composition, or the aforementioned pharmaceutical composition.

In another aspect, the present application provides the compound of formula (I), the compound of formula (II), the compound of formula (III), the compound of formula (IV), the compound of formula (V) or the compound of formula (VI) or the crystalline form thereof described above, or the aforementioned crystalline composition, or the aforementioned pharmaceutical composition for use in treating or preventing an IRAK4-related disease. In some embodiments of the present application, the mammal is a human.

The present application also provides a method for preparing the compound of formula (I), comprising the following synthetic route:

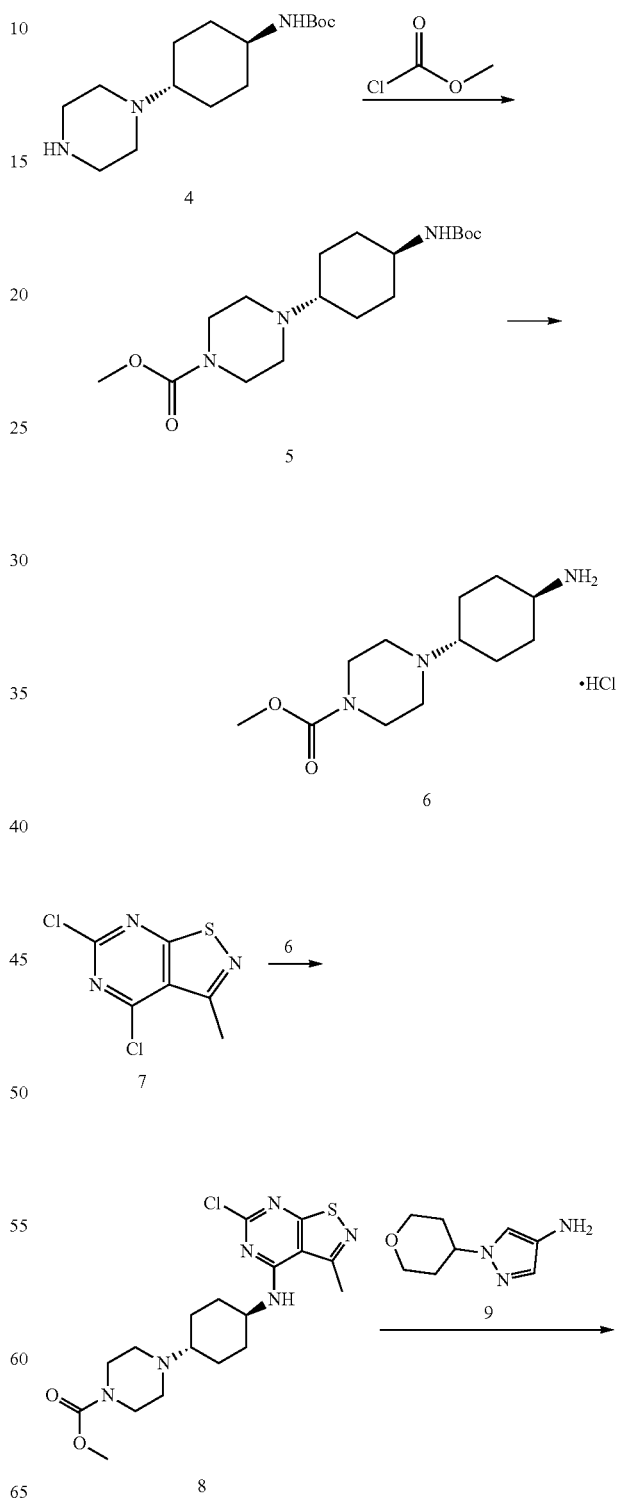

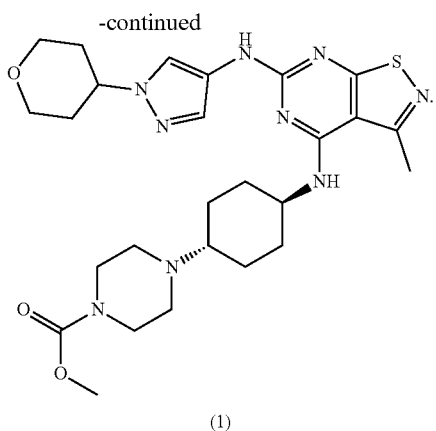

(1)

In the present application, the pharmaceutical composition can be formulated into a certain dosage form, and the administration route is preferably oral administration, parenteral administration (including subcutaneous, intramuscular and intravenous administration), rectal administration, and the like. For example, suitable dosage forms for oral administration include tablets, capsules, granules, pulvises, pills, powders, pastilles, syrups or suspensions; suitable dosage forms for parenteral administration include aqueous or non-aqueous solutions or emulsions for injection; suitable dosage forms for rectal administration include suppositories with hydrophilic or hydrophobic carriers. The dosage forms may also be formulated as desired for rapid, delayed or modified release of the active ingredient.

The crystalline form described herein may be present in the form of a non-solvate or a solvate, for example, a hydrate.

In the present application, the X-ray powder diffraction pattern of a sample is determined in the following conditions: instrument: Bruker D8 advance X-ray diffractometer; target: Cu:Kα; wavelength k=1.54056 Å; range of 2θ: 4-40°; scattering slit: 0.6 mm; detector slit: 10.5 mm; anti-scatter slit: 7.10 mm; Cu-target tube voltage and current: 40 kV, 40 mA; step size: 0.02°; step time: 0.12 s; rotation speed of sample plate: 15 rpm.

In the present application, the DSC pattern is determined in the following conditions: instrument: TA Q2000 differential scanning calorimeter; temperature range: 30-300° C.; heating rate: 10° C./min.

In the present application, TGA thermogravimetric analysis is determined in the following conditions: instrument: TA Q5000 thermogravimetric analyzer; flow rate: 25 m/min; temperature range: 30-350° C.; heating rate: 10° C./min.

It should be noted that in the X-ray powder diffraction pattern, the position and relative intensity of a peak may vary due to measuring instruments, measuring methods/conditions, and other factors. For any specific crystalline form, the position of a peak may have an error, and the measurement of 2θ has an error of 0.2°. Therefore, this error should be considered when determining each crystalline form, and crystalline forms within this margin of error are within the scope of the present application.

It should be noted that, for the same crystalline form, the position of an endothermic peak in the DSC pattern may vary due to measuring instruments, measuring methods/conditions, and other factors. For any specific crystalline form, the position of an endothermic peak may have an error of 5° C. Therefore, this error should be considered when determining each crystalline form, and crystalline forms within this margin of error are within the scope of the present application.

It should be noted that, for the same crystalline form, the position of a weight loss temperature in the TGA pattern may vary due to measuring instruments, measuring methods/conditions, and other factors. For any specific crystalline form, the weight loss temperature may have an error of 3° C. Therefore, this error should be considered when determining each crystalline form, and crystalline forms within this margin of error are within the scope of the present application.

TECHNICAL EFFECTS

The salt or crystalline form described in the present application has good solubility, better pharmacokinetic (PK) property, stable crystallization, good hygroscopicity, small influence of light and high thermal stability.

DEFINITIONS AND DESCRIPTION

Unless otherwise stated, the following terms and phrases used herein are intended to have the following meanings. A particular term or phrase, unless otherwise specifically defined, should not be considered as uncertain or unclear, but construed according to its common meaning. When referring to a trade name, it is intended to refer to its corresponding commercial product or its active ingredient.

"Mammal" includes human, domestic animals such as laboratory mammals and domestic pets (e.g., cat, dog, pig, cow, sheep, goat, horse, rabbit), and non-domesticated mammals such as wild mammals.

The term "pharmaceutical composition" refers to a formulation of the compound disclosed herein with a vehicle commonly recognized in the art for delivering a biologically active compound to a mammal, such as a human. The vehicle includes all pharmaceutically acceptable carriers for its use. The pharmaceutical composition facilitates administration of the compound to an organism.

The term "therapeutically effective amount" refers to an amount of a drug or a medicament that is sufficient to provide the desired effect but is non-toxic. The determination of the effective amount varies from person to person. It depends on the age and general condition of a subject, as well as the particular active substance used. The appropriate effective amount in a case may be determined by those skilled in the art in the light of routine tests.

The term "treat" or "treatment" means administering the compound or formulation described in the present application to ameliorate or eliminate a disease or one or more symptoms associated with the disease, and includes:
  (i) inhibiting a disease or disease state, i.e., arresting its development; and
  (ii) alleviating a disease or disease state, i.e., causing its regression.

The term "prevent" or "prevention" means administering the compound or formulation described herein to prevent a disease or one or more symptoms associated with the disease, and includes: preventing the occurrence of the disease or disease state in a mammal, particularly when such a mammal is predisposed to the disease state but has not yet been diagnosed with it.

The term "pharmaceutically acceptable carriers" refers to those which are administered together with the active ingredient, do not have a significant irritating effect on an organism and do not impair the biological activity and properties of the active compound. For additional information on carriers, reference may be made to Remington: The Science and Practice of Pharmacy, 21st Ed., Lippincott, Williams & Wilkins (2005), the content of which is incorporated herein by reference.

In the present application, "eq" represents a molar equivalent.

In the present application, "FA" represents trifluoroacetic acid.

The word "comprise" and variations thereof such as "comprises" or "comprising" will be understood in an open, non-exclusive sense, i.e., "including but not limited to".

The compounds of the present application can be prepared using a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples of the present application.

The chemical reactions of the embodiments disclosed herein are carried out in a proper solvent that must be suitable for the chemical changes in the present application and the reagents and materials required. In order to acquire the compounds disclosed herein, it is sometimes necessary for those skilled in the art to modify or select a synthesis procedure or a reaction scheme based on the existing embodiments.

All solvents used in the present application are commercially available and can be used without further purification. The solvents used in the present application are commercially available, and supplier's catalog names are given for commercially available compounds. Adding a mixed solvent into the reaction solution means that the solvents may be mixed first and then the mixed solvent is added into the reaction solution; or each single solvent is added into the reaction solution in sequence and is mixed in the reaction system.

Compounds are named according to conventional nomenclature rules in the art or using ChemDraw® software, and supplier's catalog names are given for commercially available compounds.

DETAILED DESCRIPTION

Figure 1:
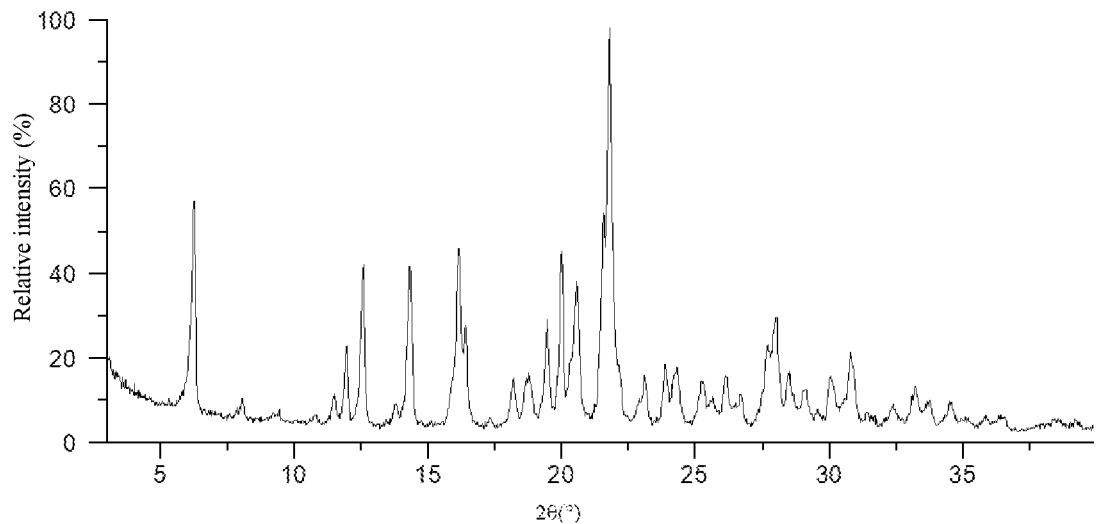
FIG. 1 is an XRPD pattern of the crystalline form A of the compound of formula (II) using Cu Kα radiation.
Figure 2:
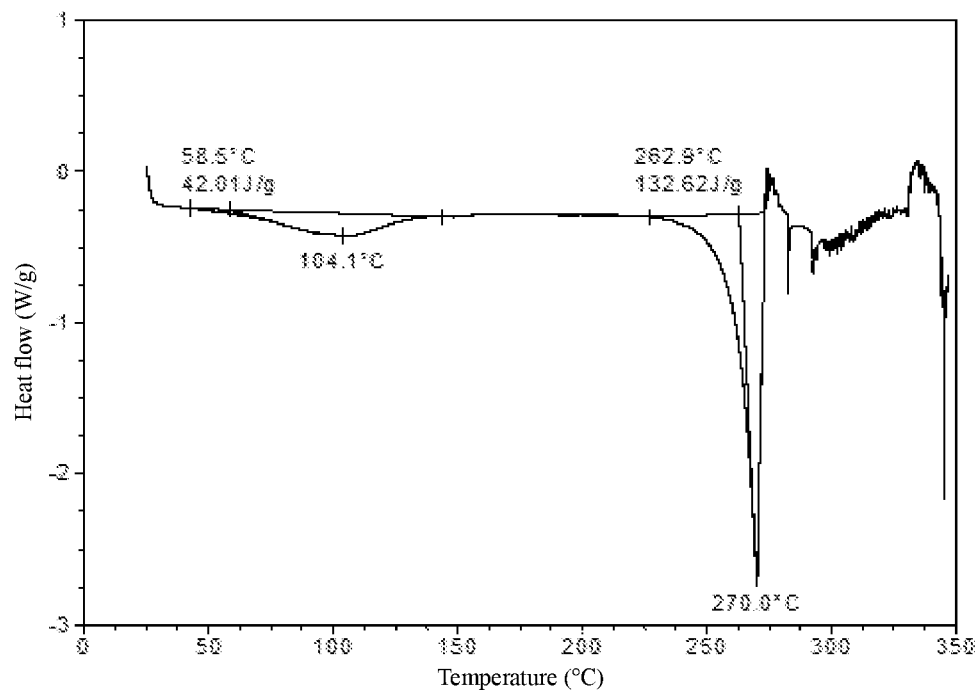
FIG. 2 is a DSC pattern of the crystalline form A of the compound of formula (II)
Figure 3:
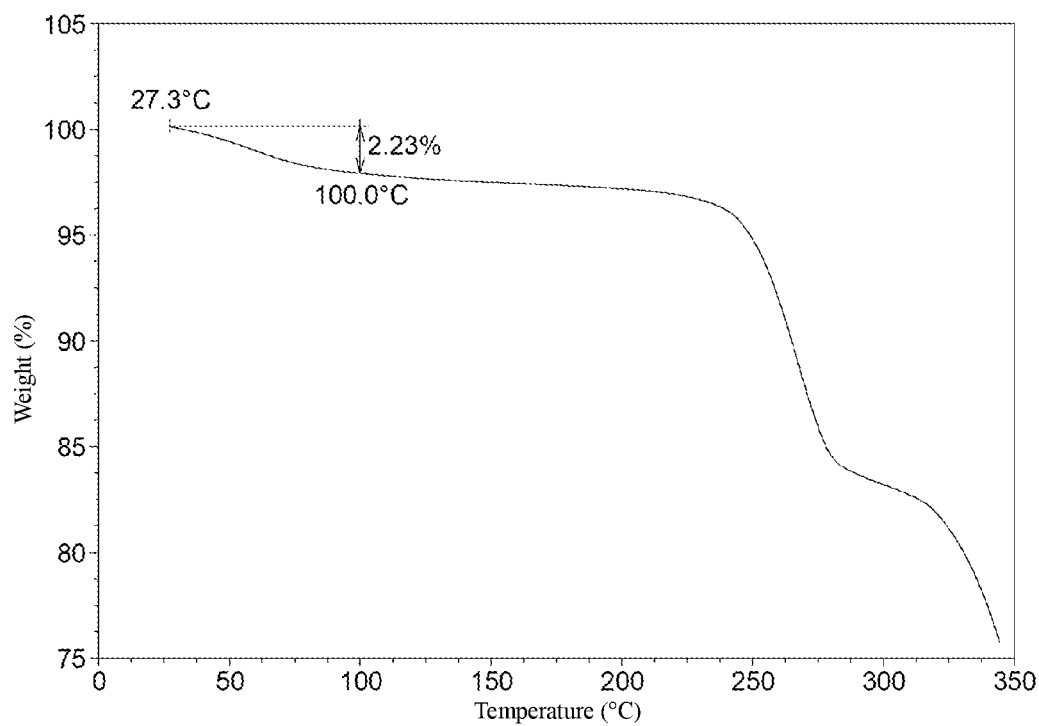
FIG. 3 is a TGA pattern of the crystalline form A of the compound of formula (II)
Figure 4:
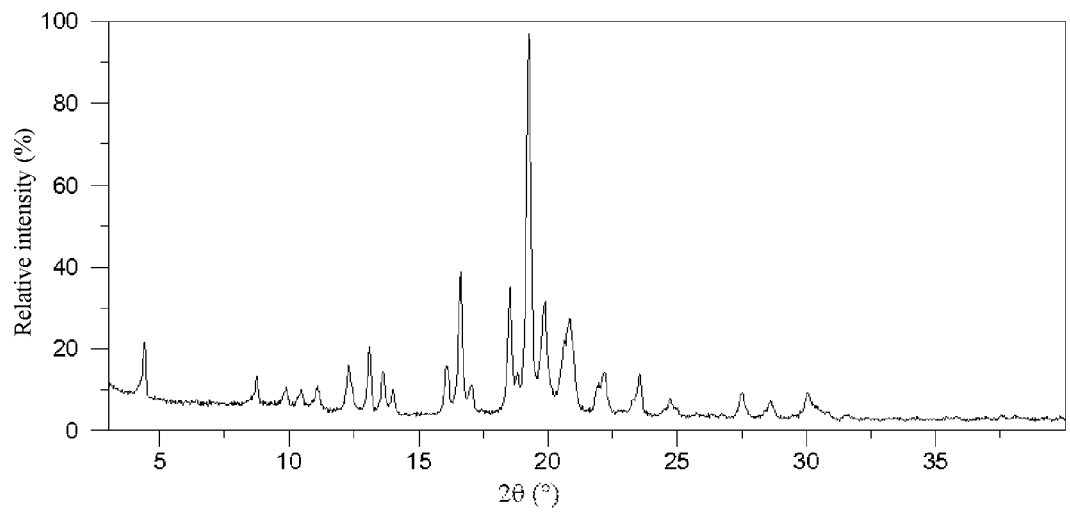
FIG. 4 is an XRPD pattern of the crystalline form A of the compound of formula (I) using Cu Kα radiation.
Figure 5:
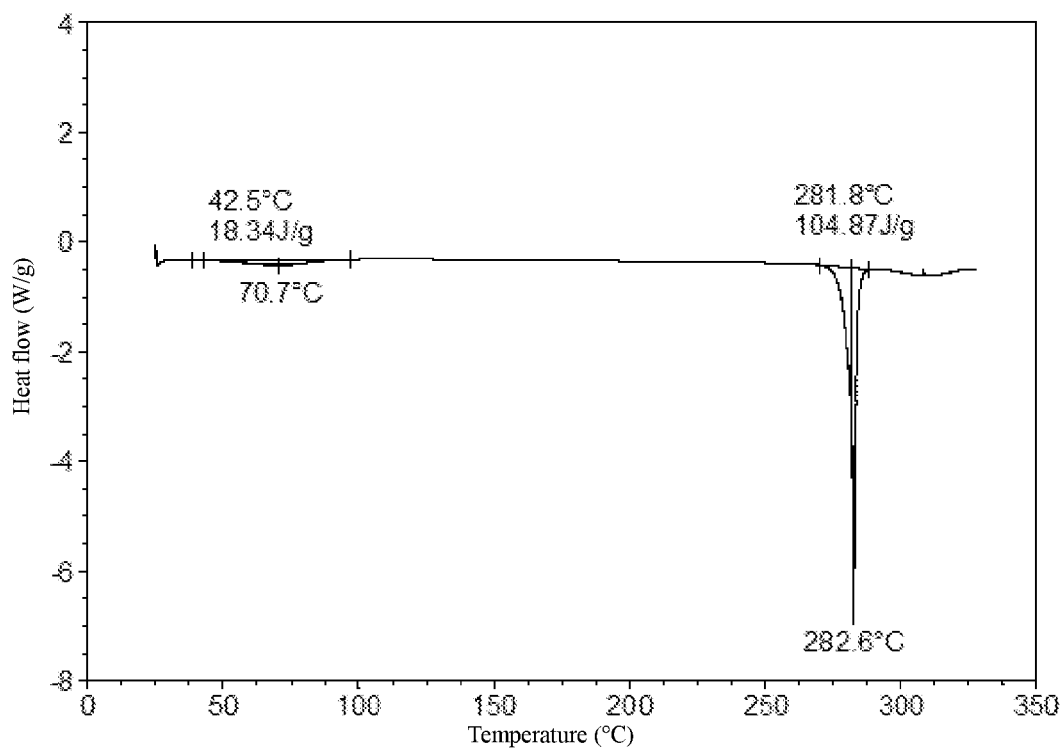
FIG. 5 is a DSC pattern of the crystalline form A of the compound of formula (I)
Figure 6:
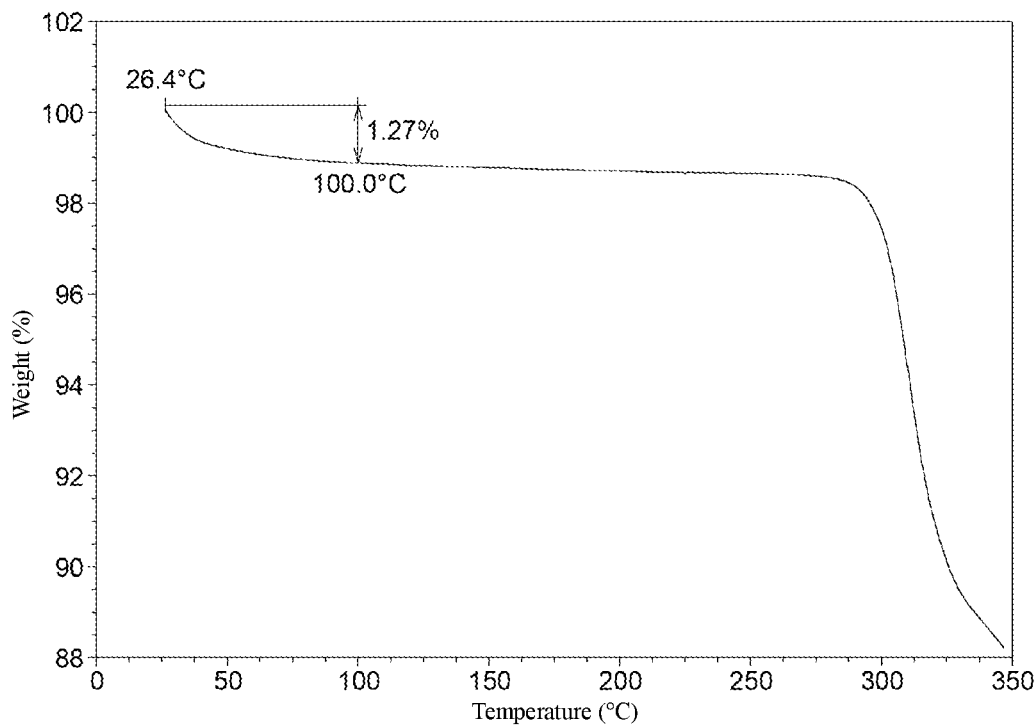
FIG. 6 is a TGA pattern of the crystalline form A of the compound of formula (I)
Figure 7:
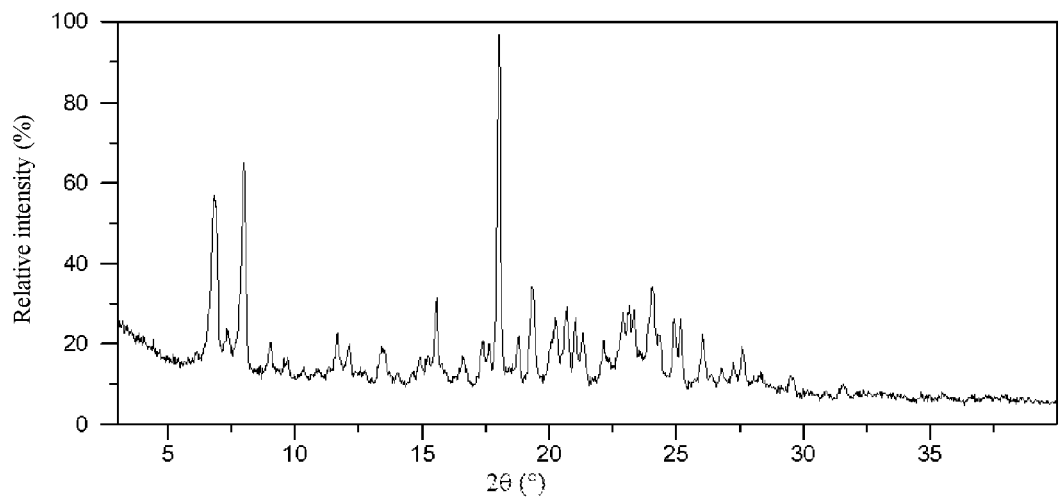
FIG. 7 is an XRPD pattern of the crystalline form A of the compound of formula (III) using Cu Kα radiation.
Figure 8:
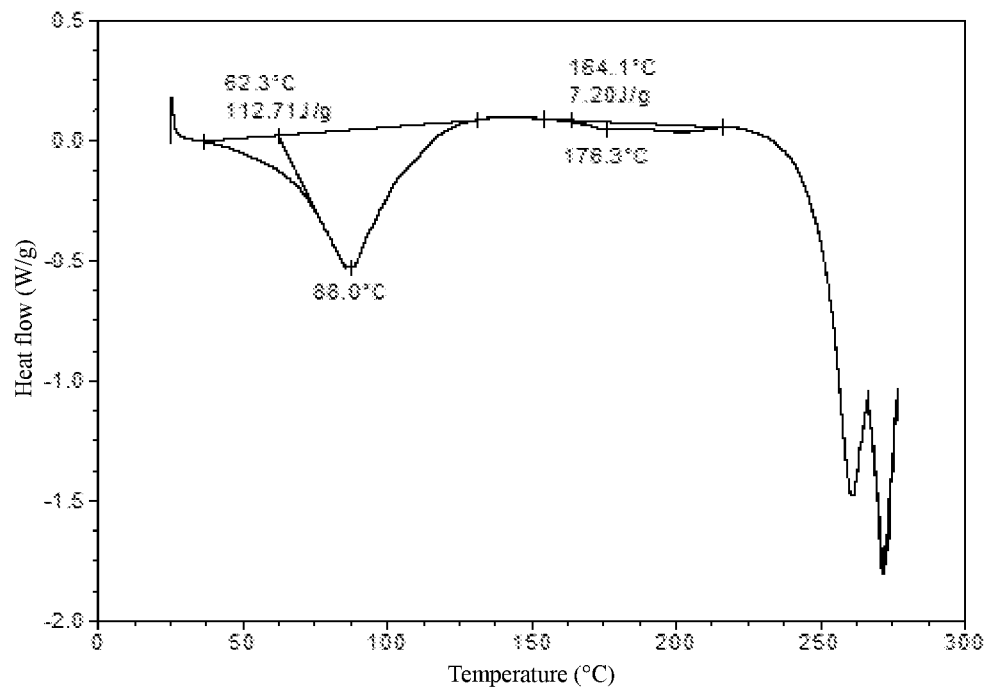
FIG. 8 is a DSC pattern of the crystalline form A of the compound of formula (III)
Figure 9:
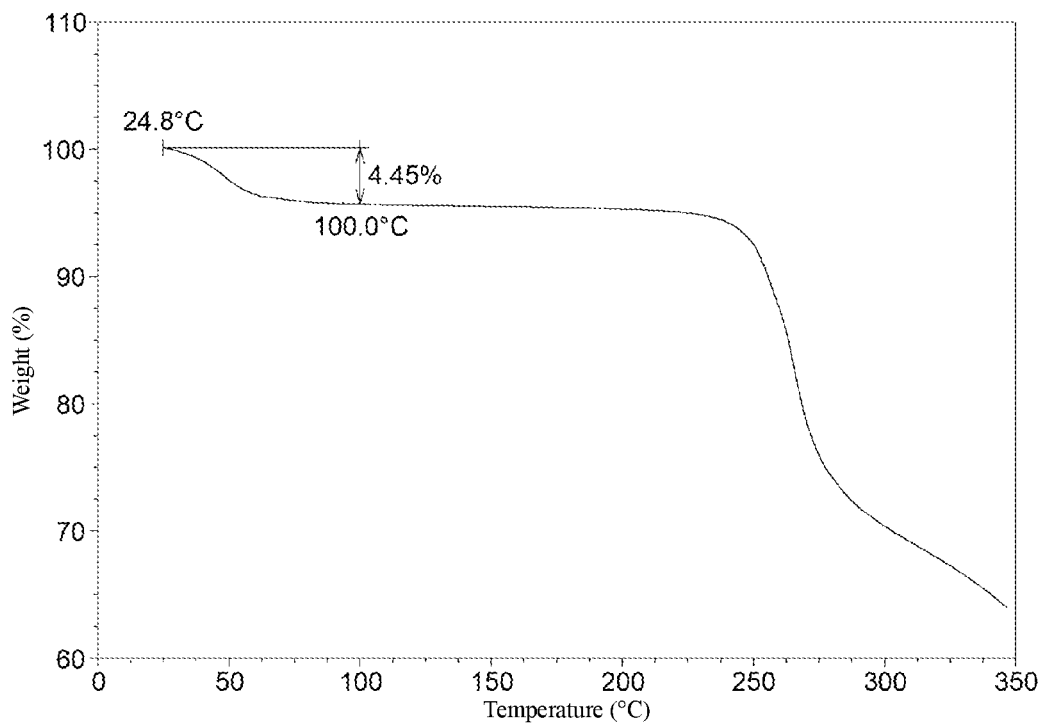
FIG. 9 is a TGA pattern of the crystalline form A of the compound of formula (III)
Figure 10:
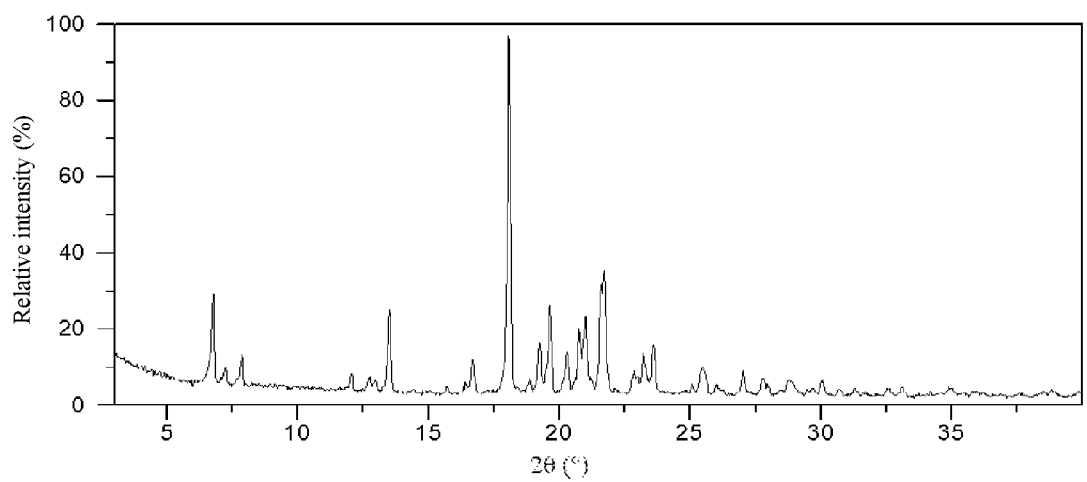
FIG. 10 is an XRPD pattern of the crystalline form A of the compound of formula (IV) using Cu Kα radiation.
Figure 11:
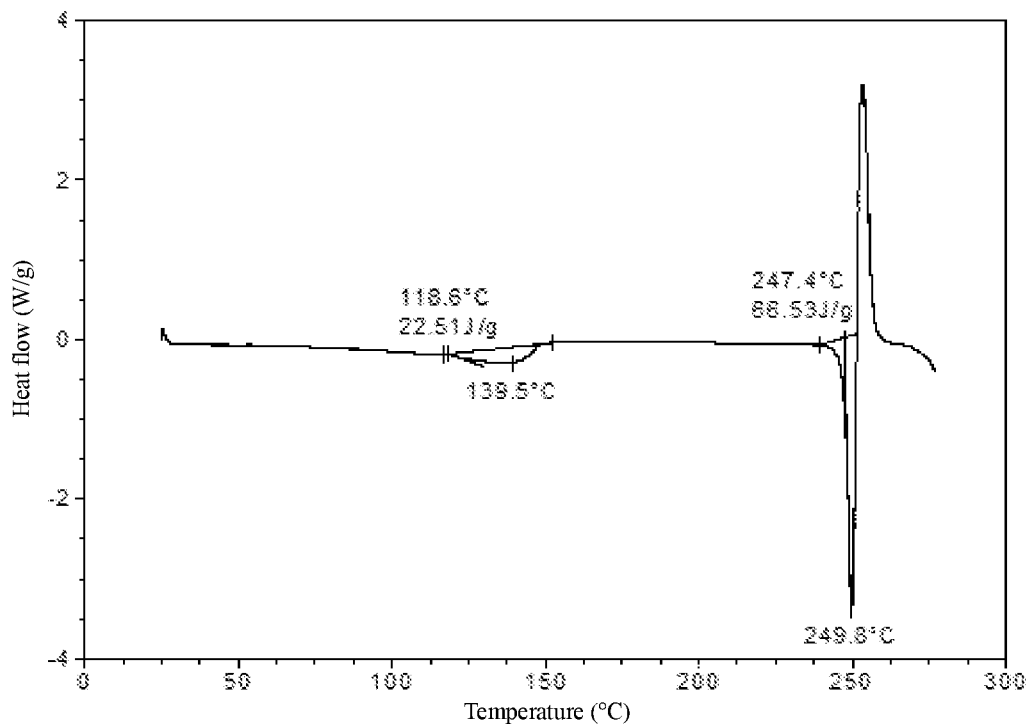
FIG. 11 is a DSC pattern of the crystalline form A of the compound of formula (IV)
Figure 12:
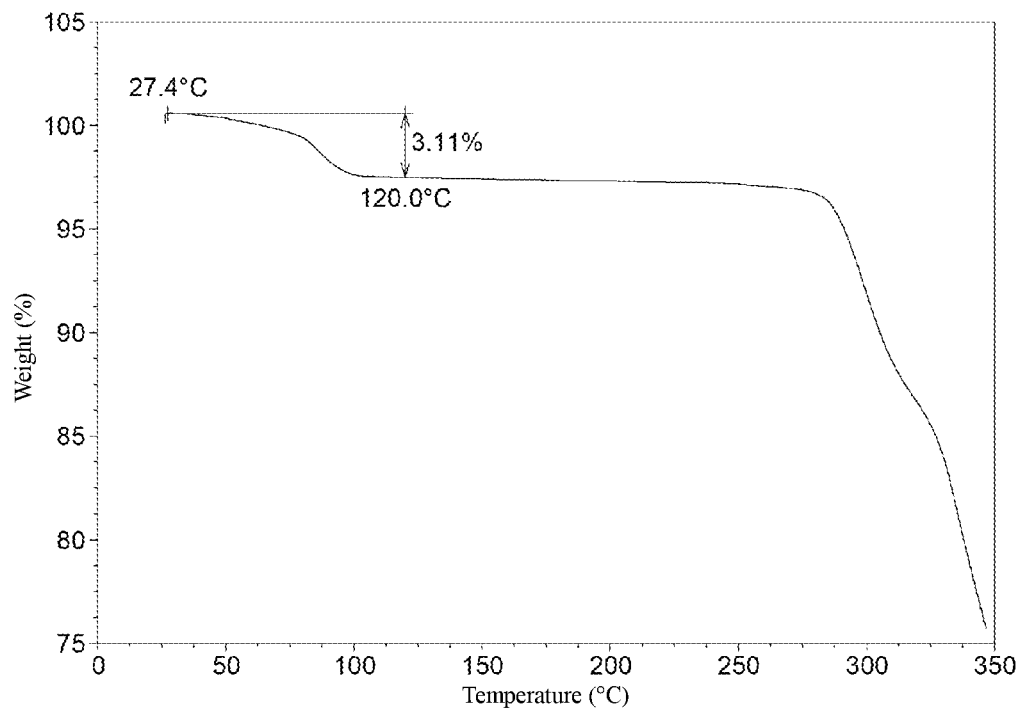
FIG. 12 is a TGA pattern of the crystalline form A of the compound of formula (IV)
Figure 13:
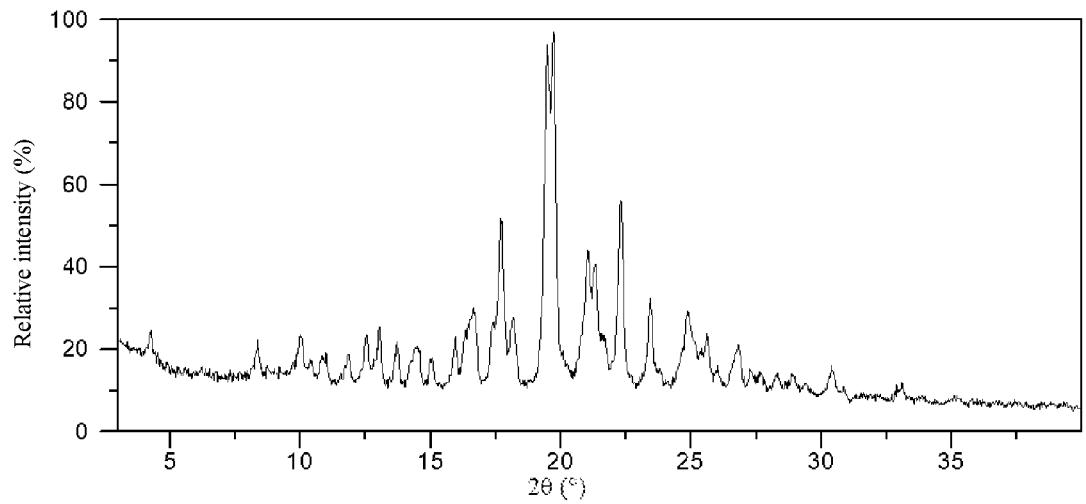
FIG. 13 is an XRPD pattern of the crystalline form A of the compound of formula (V) using Cu Kα radiation.
Figure 14:
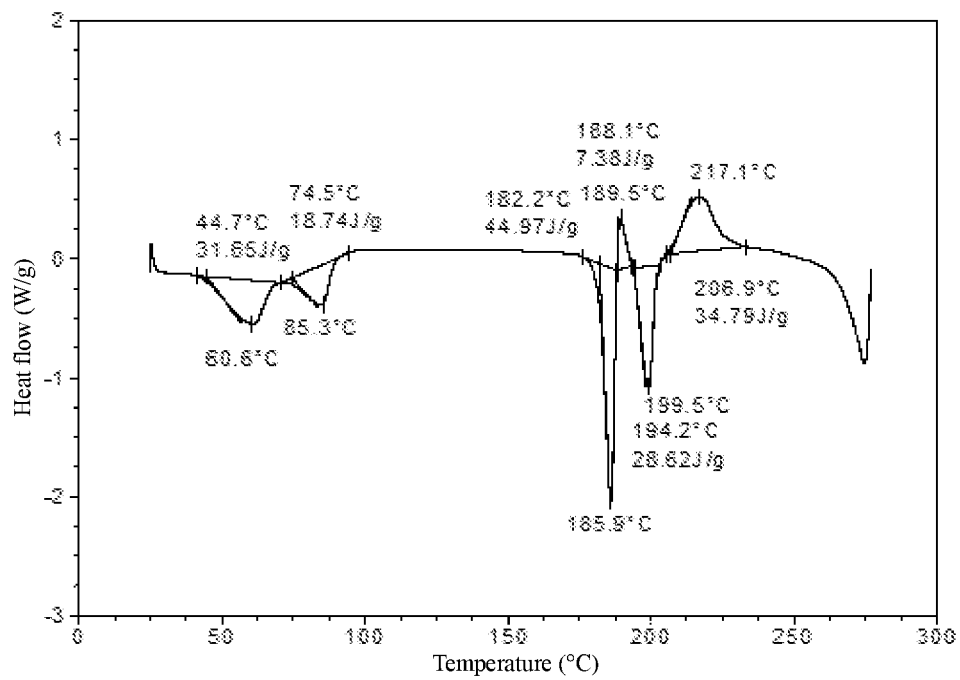
FIG. 14 is a DSC pattern of the crystalline form A of the compound of formula (V)
Figure 15:
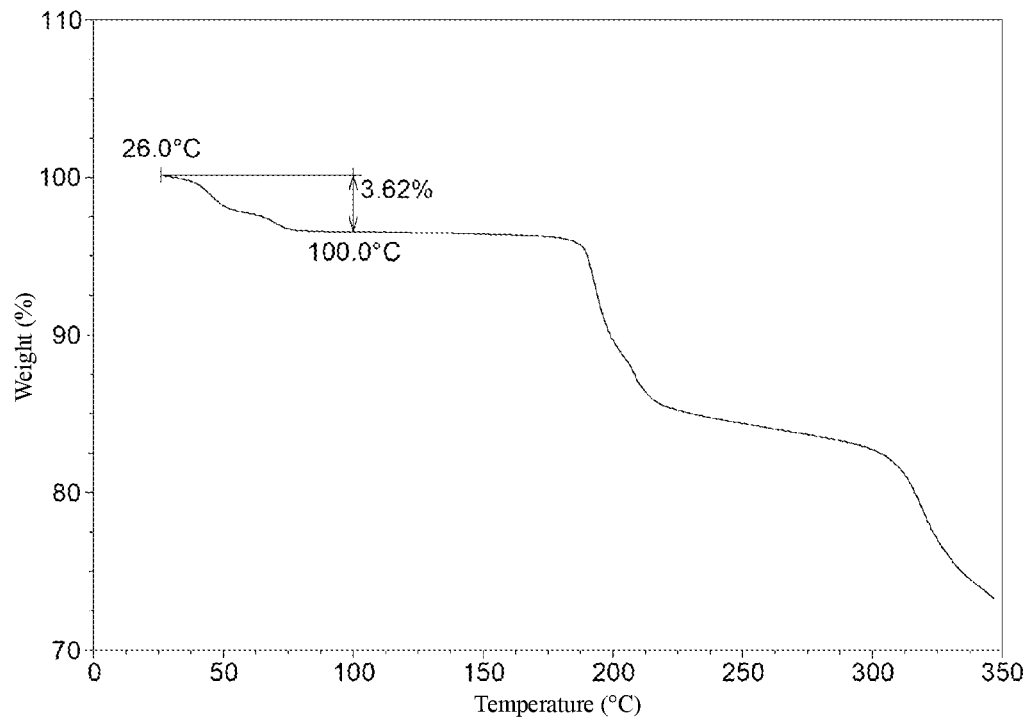
FIG. 15 is a TGA pattern of the crystalline form A of the compound of formula (V)
Figure 16:
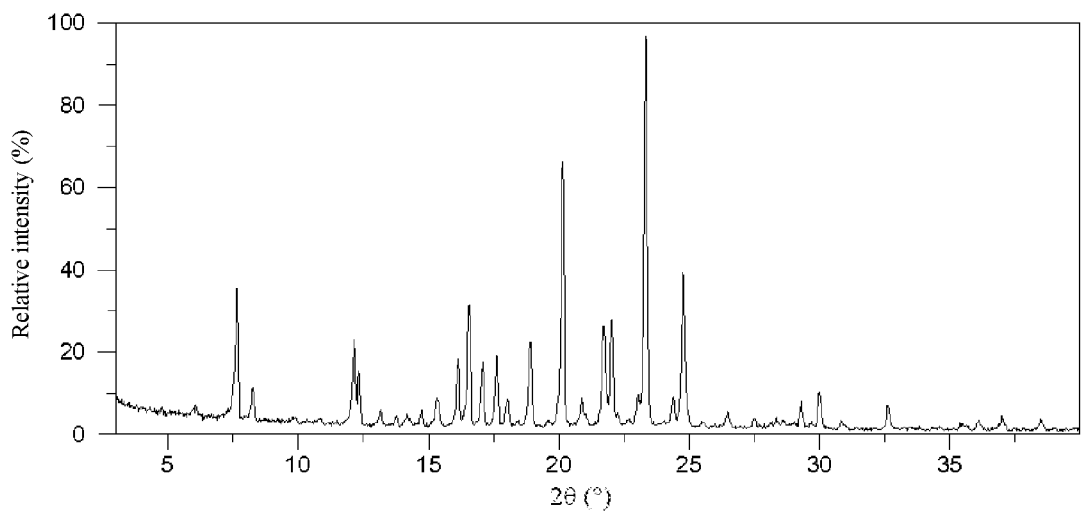
FIG. 16 is an XRPD pattern of the crystalline form A of the compound of formula (VI) using Cu Kα radiation.
Figure 17:
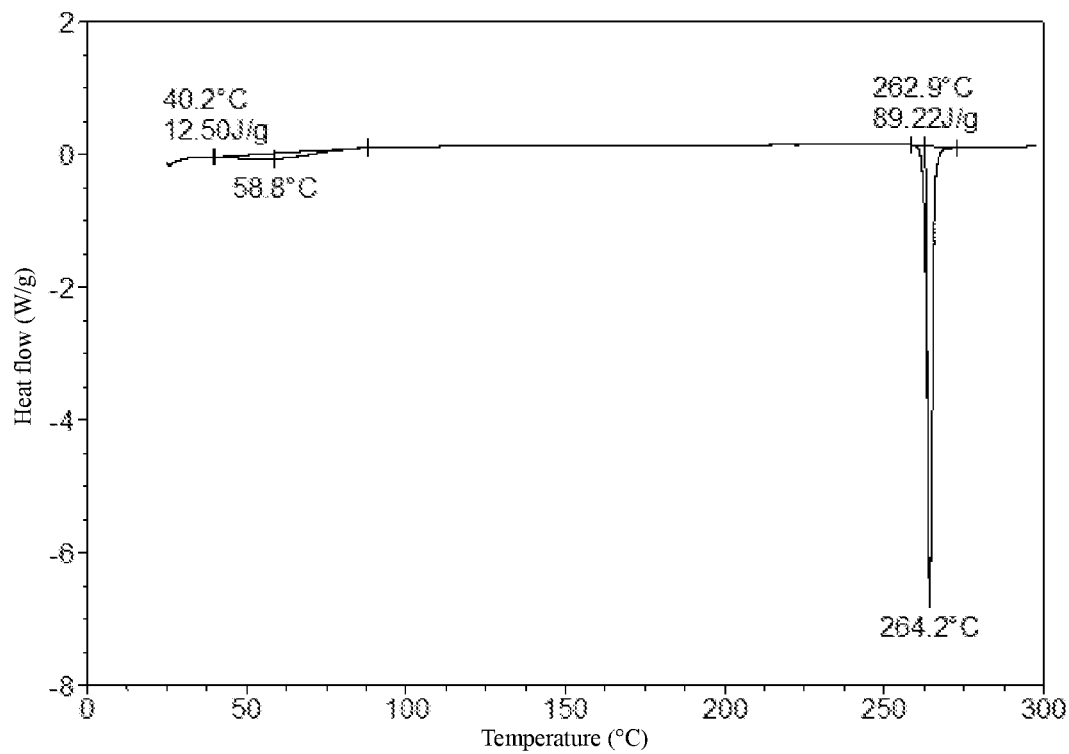
FIG. 17 is a DSC pattern of the crystalline form A of the compound of formula (VI)
Figure 18:
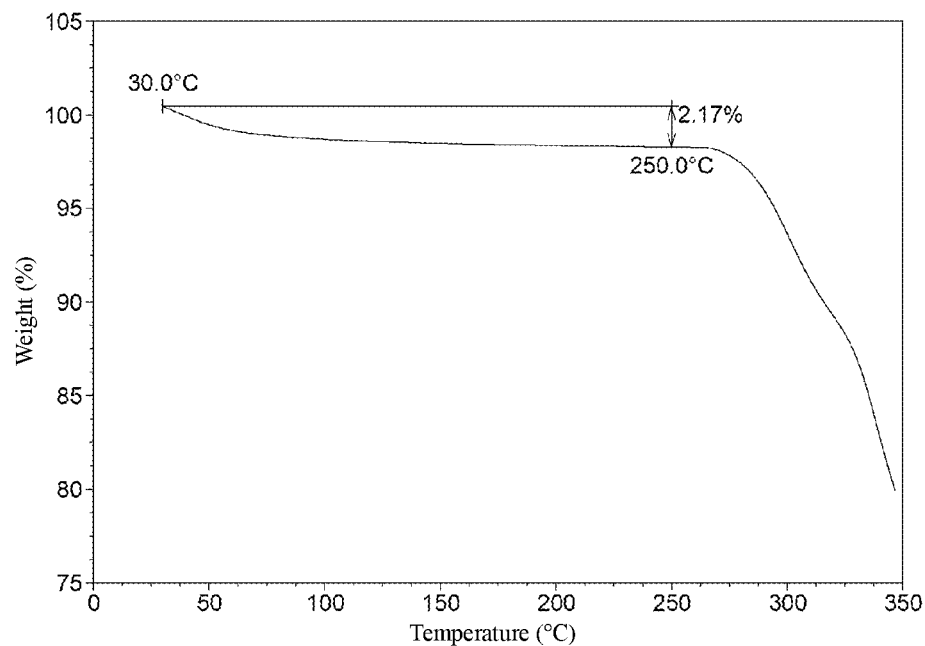
FIG. 18 is a TGA pattern of the crystalline form A of the compound of formula (VI).

The present application is described in detail below by way of examples. However, this is by no means disadvantageously limiting the scope of the present application. Although the present application has been described in detail herein and specific embodiments have also been disclosed, it will be apparent to those skilled in the art that various changes and modifications can be made to the specific embodiments without departing from the spirit and scope of the present application.

Example 1: Preparation of the Compound of Formula (I)

Synthetic Route:

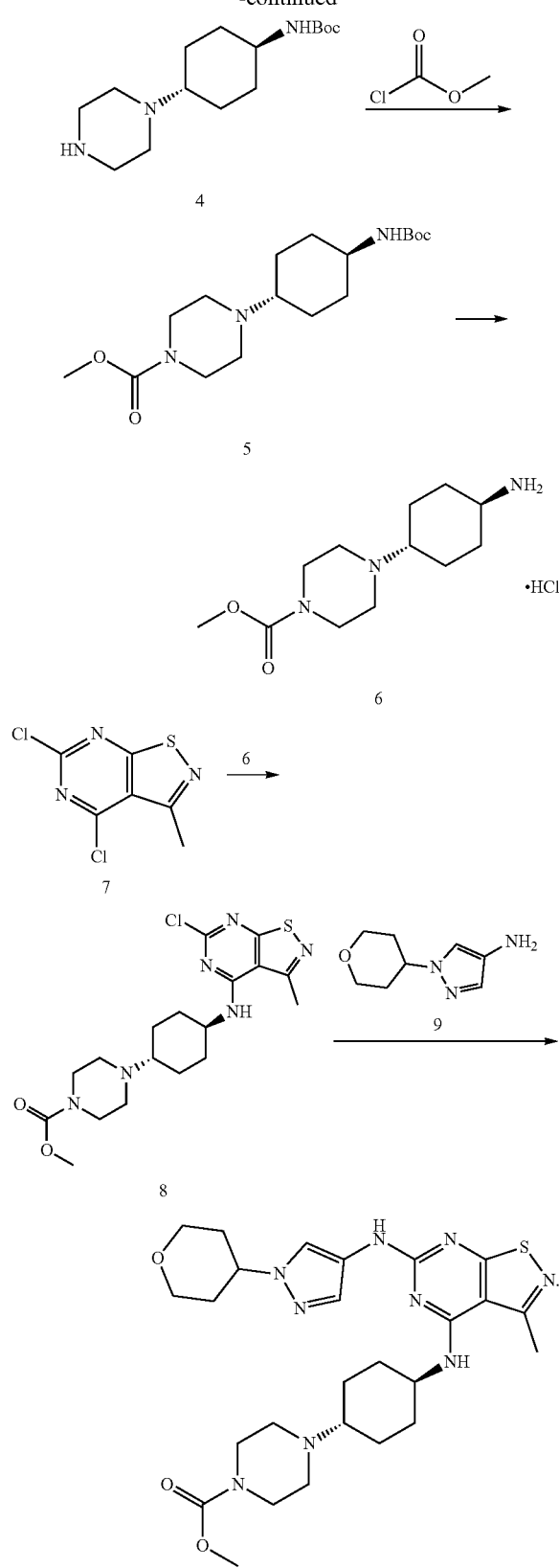

Step 1

Compound 2 (100.0 g, 466.6 mmol) was added to a flask containing isopropanol (1.5 L), followed by the addition of compound 1 (125.3 g, 466.6 mmol) and sodium bicarbonate (156.8 g, 1.9 mol) to the reaction system, and the reaction system was stirred at 90° C. (internal temperature) for 12 h. After the starting materials were consumed completely as detected by LCMS, the reaction system was cooled to 50° C. and filtrated, and then the filter cake was rinsed with 1 L of tetrahydrofuran; the organic phase was concentrated under reduced pressure to dryness. The crude product was homogenized with methyl tert-butyl ether:petroleum ether=2:1 (800.0 mL) and filtered, and the filter cake was rinsed with methyl tert-butyl ether (50.0 mL×2), and concentrated to remove the solvent to give compound 3.

LCMS (ESI) m/z: 374.3[M+H]$^+$ $^1$H NMR (400 MHz, CDCl$_3$) δ 7.27-7.34 (m, 5H), 4.36 (s, 1H), 3.53 (s, 1H), 3.38 (s, 1H), 2.22-2.60 (m, 8H), 2.20-2.22 (m, 1H), 2.06-2.09 (m, 2H), 1.92-1.95 (m, 2H), 1.40-1.46 (m, 9H), 1.30-1.36 (m, 3H), 1.10-1.17 (m, 2H).

Step 2

In argon atmosphere, palladium hydroxide (31.2 g, 44.4 mmol) was added slowly in portions into hydrogenation flask, and meanwhile, ethanol (800 mL) was added slowly in argon atmosphere, followed by the addition of compound 3 (78.0 g, 208.8 mmol) into the reaction system; the reaction system was stirred at 50° C. for 2 h at 50 Psi hydrogen pressure. After the starting materials were consumed completely as detected by LCMS, the reaction solution was filtered through diatomite, the filter cake was rinsed with the ethanol (5.0 L), and the filtrate was concentrated under reduced pressure to give compound 4.

LCMS (ESI) m/z: 284.2 [M+H]$^+$ $^1$H NMR (400 MHz, CDCl$_3$) δ 4.29-4.47 (m, 1H), 3.25-3.46 (m, 1H), 2.79-2.98 (m, 4H), 2.43-2.62 (m, 4H), 2.13-2.25 (m, 1H), 1.98-2.11 (m, 2H), 1.83-1.95 (m, 2H), 1.65-1.71 (m, 1H), 1.39-1.57 (m, 9H), 1.23-1.38 (m, 2H), 1.03-1.17 (m, 2H).

Step 3

Compound 4 (150.0 g, 529.3 mmol) and sodium bicarbonate (33.4 g, 1.6 mol) were added into tetrahydrofuran (1.5 mL) and water (800.0 mL), the mixture was cooled to 0° C., and methyl chloroformate (295.5 g, 3.1 mol) was added dropwise to the reaction system; the reaction system was stirred at 25° C. for 0.5 h, and the reaction was completed as detected by LCMS. Ethyl acetate (500.0 mL) and water (500.0 mL) were added into the reaction solution for extraction and separation, an aqueous phase was extracted with ethyl acetate (500.0 mL), organic phases were combined, and the organic phases were dried over anhydrous sodium sulfate, filtered and concentrated under reduced pressure to give compound 5.

LCMS (ESI) m/z: 342.3 [M+H]$^+$ $^1$H NMR (400 MHz, CDCl$_3$) δ 4.31-4.44 (m, 1H), 3.66-3.74 (m, 3H), 3.44-3.58 (m, 4H), 3.25-3.42 (m, 1H), 2.46-2.58 (m, 4H), 2.20-2.32 (m, 1H), 2.02-2.11 (m, 2H), 1.81-1.93 (m, 2H), 1.51-1.81 (m, 9H), 1.26-1.40 (m, 2H), 1.01-1.21 (m, 2H).

Step 4

Compound 5 (100.0 g, 292.9 mmol) was added into methanol (1.0 L), 4 M hydrochloric acid/methanol (732.2 mL) was added into the reaction system, and the reaction system was stirred at 25° C. for 4 h. The reaction was completed as detected by TLC and LCMS, and the reaction solution was concentrated under reduced pressure to give compound 6.

LCMS (ESI) m/z: 242.1 [M+H]$^+$

Step 5

Compound 7 (40.0 g, 181.8 mmol), sodium carbonate (77.1 g, 727.0 mmol) and compound 6 (60.6 g, 218.1 mmol) were added into a reaction flask containing acetonitrile (600.0 mL), and the reaction system was stirred at 80° C. for 12 h. After the starting materials were consumed completely as detected by LCMS, the reaction solution was concentrated under reduced pressure, dichloromethane (1.0 L) and water (1.0 L) were added into a flask containing the crude products for extraction and separation, the aqueous phase was extracted once with dichloromethane (1.0 L), and the organic phases were combined, dried over anhydrous sodium sulfate, filtered and concentrated under reduced pressure to give compound 8.

LCMS (ESI) m/z: 425.3 [M+H]$^+$ $^1$H NMR (400 MHz, DMSO-d$_6$) δ 6.97-7.03 (m, 1H), 4.03-4.14 (m, 1H), 3.55-3.63 (m, 3H), 3.33-3.39 (m, 6H), 2.75-2.83 (m, 3H), 2.40-2.48 (m, 2H), 2.28-2.39 (m, 1H), 1.93-2.02 (m, 2H), 1.78-1.88 (m, 2H), 1.52-1.65 (m, 2H), 1.30-1.45 (m, 2H).

Step 6

Compound 8 (70.0 g, 164.7 mmol), compound 9 (30.3 g, 181.2 mmol) and p-toluenesulfonic acid monohydrate (109.7 g, 576.5 mmol) were sequentially added into a reaction flask containing dioxane (1.1 L), and the reaction system was stirred at 100° C. for 10 h. After the starting materials were consumed completely as detected by LCMS, the reaction solution was concentrated under reduced pressure to remove the dioxane, water (550.0 mL) was added into the reaction solution until the materials were completely dissolved, saturated sodium hydroxide solution was added into the reaction system under stirring until pH=11-12, and a large amount of solid was precipitated; the reaction system was stirred at room temperature for 30 min and filtered, and the filter cake was rinsed with water (500 mL) and concentrated under reduced pressure to remove excessive water to give the compound of formula (I). LCMS (ESI) m/z: 556.4 [M+H]$^+$ Example 2: Preparation of Crystalline Form A of the Compound of Formula (II)

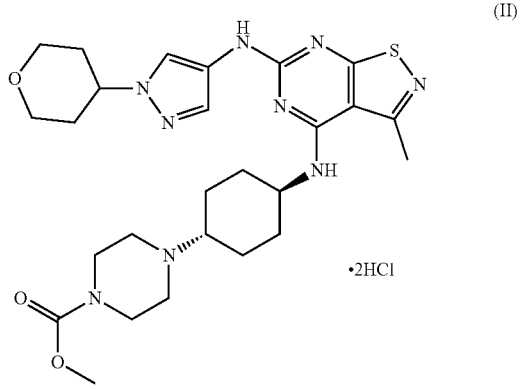 [SMILES: COC(=O)N1CCN([C@H]2CC[C@H](Nc3nc(Nc4cnn(C5CCOCC5)c4)nc4snc(C)c34)CC2)CC1]

(II)

Methanol (600 mL) and 4 mol/L hydrochloric acid methanol solution (108 mL) were added into a reaction flask containing the compound of formula (I)(60.0 g, 108.0 mmol), the reaction system was stirred at 25° C. for 1 h, then a large amount of solid was precipitated, the reaction solution was filtered, and the filter cake was rinsed with ethyl acetate (200.0 mL) and dried to remove excessive methanol, to give the crystalline form A of the compound of formula (II).

$^1$H NMR (400 MHz, DMSO-d$_6$) δ=11.35 (brs, 1H), 9.29 (s, 1H), 7.92 (s, 1H), 7.60 (s, 1H), 6.33-6.22 (m, 1H), 4.44-4.37 (m, 1H), 4.18-4.05 (m, 3H), 4.04-3.93 (m, 2H), 3.71 (s, 3H), 3.68-3.63 (m, 5H), 3.28-2.99 (m, 4H), 2.71 (s, 3H), 2.33-2.19 (m, 4H), 2.05-1.85 (m, 4H), 1.77-1.54 (m, 4H).

The content of Cl ion in the crystalline form A of the compound of formula (II) was 11% by IC (ion chromatography) test, and N=2 was calculated according to the IC calculation formula=N×Cl (M.W)/[compound of formula (I) (M.W)±N×Cl (M.W)/]=11%, thus determining that the crystalline form A of the compound of formula (II) contains two molecules of hydrochloric acid.

Example 3: Preparation of Crystalline Form A of the Compound of Formula (I)

The compound crystalline form A of the compound of formula (II) (6.2 g, 9.9 mmol) was added into 50 mL of water, the reaction system was added with saturated aqueous sodium carbonate solution to adjust pH=8 and extracted with dichloromethane (50 mL×4), and the organic phases were combined, dried over anhydrous sodium sulfate, filtered and concentrated under reduced pressure; the resulting compound was added into 30 mL of methanol, the reaction system was stirred for 1 h and filtered, and the filter cake was concentrated under reduced pressure to remove the solvent, to give the crystalline form A of the compound of formula (I).

Example 4: Preparation of Crystalline Form A of the Compound of Formula (III)

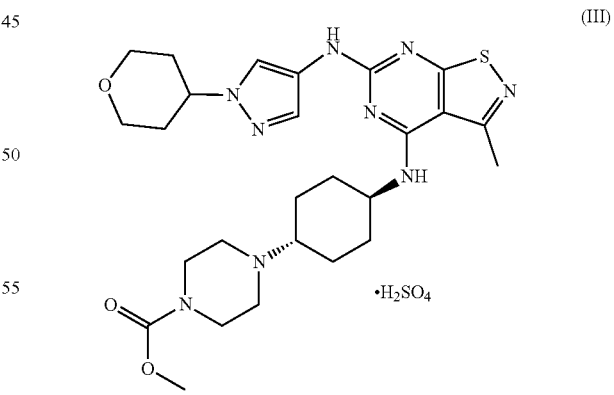

(III)

100 mg of the crystalline form A of the compound of formula (I) was weighed and added into 2 mL of anhydrous methanol at room temperature, followed by the addition of 1.1 eq of sulfuric acid; it was observed that white solid was precipitated after the mixed solution was clarified for 30 s, then the mixed system was warmed to 50° C. and stirred for 16 h after being stirred at room temperature for 4 h, and there was no significant change in the mixed system. The reaction system was cooled to room temperature, filtered and concentrated to remove the solvent, to give the crystalline form A of the compound of formula (III).

Example 5: Preparation of Crystalline Form A of the Compound of Formula (IV)

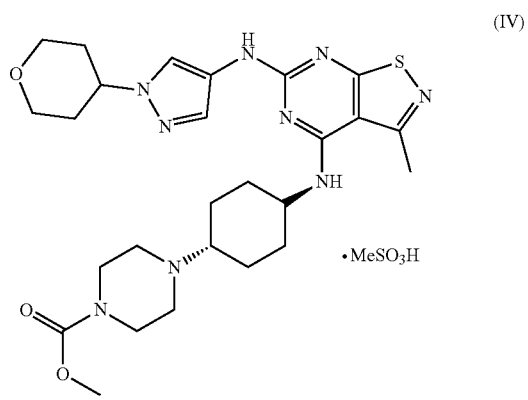

100 mg of the crystalline form A of the compound of formula (I) was weighed and added into 2 mL of anhydrous methanol at room temperature, followed by the addition of 1.1 eq of methanesulfonic acid; it was observed that there was a tiny amount of precipitation and then white solid was precipitated after 5 min in the mixed solution, then the mixed system was warmed to 50° C. and stirred for 16 h after being stirred at room temperature for 4 h, and there was no significant change in the mixed system. The reaction system was cooled to room temperature, filtered and concentrated to remove the solvent, to give the crystalline form A of the compound of formula (IV).

Example 6: Preparation of Crystalline Form A of the Compound of Formula (V)

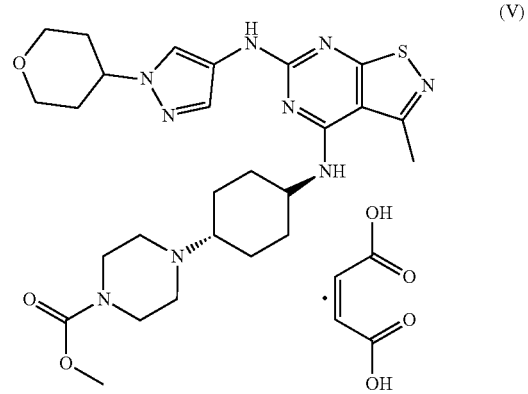

100 mg of the crystalline form A of the compound of formula (I) was weighed and added into 2 mL of anhydrous methanol at room temperature, followed by the addition of 1.1 eq of maleic acid; it was observed that there was a tiny amount of precipitation and then white solid was precipitated after 30 s in the mixed solution, then the mixed system was warmed to 50° C. and stirred for 16 h after being stirred at room temperature for 4 h, and there was no significant change in the mixed system. The reaction system was cooled to room temperature, filtered and concentrated to remove the solvent, to give the crystalline form A of the compound of formula (V).

Example 7: Preparation of Crystalline Form A of the Compound of Formula (VI)

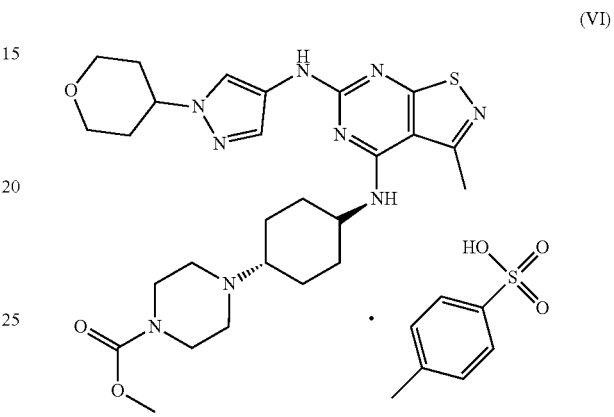

500 mg of the crystalline form A of the compound of formula (I) was weighed and added into 5 mL of anhydrous methanol at room temperature, followed by the addition of 1.1 eq of p-toluenesulfonic acid. It was observed that the mixed solution became clear one minute after addition of p-toluenesulfonic acid, and the white solid was precipitated after about 30 s. After being reacted at 25° C. for 4 h, the mixed solution was heated to 50° C. and become clear after being stirred for 12 h, and the white solid was precipitated after the mixed solution was continuous stirred for 24 h. The reaction system was cooled to room temperature, filtered and concentrated to remove the solvent, to give the crystalline form A of the compound of formula (VI).

Example 8: Study of Polycrystalline Forms

According to Table 7, the crystalline form A of the compound formula (II) was weighed and added into 5 mL of reaction flasks, and the single solvents or mixed solvents shown in Table 7 were added to the flasks to form suspensions. Then, samples of the aforementioned suspensions were stirred for 2 days on a constant-temperature heating stirrer at 50° C. The reaction system was cooled to room temperature, filtered and concentrated to remove the solvent, to give samples, and XRPD testing was performed on the samples.

TABLE 7

Solution suspension crystallization method for study in poly crystaltine forms

| No. | Solvent | Mass of | Volume of |
|---|---|---|---|
| 1 | Methanol | 100.3 mg | 2.0 |
| 2 | Ethanol | 100.1 mg | 2.0 |
| 3 | Acetonitrile | 100.5 mg | 2.0 |
| 4 | Acetone | 100.7 mg | 2.0 |
| 5 | Ethyl acetate | 100.2 mg | 2.0 |
| 6 | Tetrahydrofuran | 100.5 mg | 2.0 |
| 7 | Methanol:tert-butyl methyl ether (1:1) | 100.8 mg | 2.0 |
| 8 | Tert-butyl methyl ether | 100.9 mg | 2.0 |
| 9 | Toluene | 100.3 mg | 2.0 |
| 10 | N-hexane | 100.5 mg | 2.0 |
| 11 | Methanol:water (v/v = 93/7) | 100.1 mg | 1.0 |
| 12 | Methanol:water (v/v = 85/15) | 100.5 mg | 1.0 |
| 13 | Ethanol:water (v/v = 95/5) | 100.8 mg | 1.0 |

Experimental conclusion: the XRPD results showed that the positions of diffraction peak of the above 13 samples were consistent with those of the solid crystalline form A of the compound of formula (II) in Example 2, and it was determined that all samples were the crystalline form A of the compound of formula (II).

Example 9: Studies in Equilibrium Solubility and Bio Media Solubility of Crystalline Form A of the Compound of Formula (I)

1. Equilibrium Solubility Experiment for Biological Media and pH Buffers 12 parts of about 2 mg of the crystalline form A of the compound of formula (II) were weighed and added into 2 mL of glass bottles, followed by the addition of 1 mL of media after adding magnetic stir bar; the mixture was heated and stirred at 37° C. in a stirrer, the compound was supplemented until the mixture had the solubility of 10 mg/mL if the mixture was dissolved, then the reaction system was stirred for 24 h, and the samples were taken. The taken samples were centrifuged, the supernatant of the samples was taken and diluted by a proper time after pH was determined, and the concentration of the supernatant was determined by UPLC.

2. Preparation of Diluent and Mobile Phase

Diluent: acetonitrile:water (1:1)

For example, 1 L of pure water and 1 L of pure acetonitrile were mixed in a glass bottle, degassed with ultrasonic for 20 min, and cooled to room temperature.

Mobile phase A: 0.1% aqueous FA solution

For example, 2.0 mL of FA was weighed out and added to 2000 mL of water, and the mixture was sonicated for 20 min, mixed well and cooled to room temperature as mobile phase A.

Mobile phase B: 0.1% FA ACN/MeOH (1:1) solution

For example, 1 L of methanol and 1 L of pure acetonitrile were mixed in a glass bottle, 2.0 mL of FA was weighed out and added to 2000 mL of acetonitrile/methanol (1:1) solution, and the mixture was sonicated for 20 min, mixed well and cooled to room temperature as mobile phase B.

3. Preparation of Control Solutions

Two parts of 5 mg of working reference crystalline form A of the compound of formula (II) were accurately weighed and added into sample bottles, followed by the addition of 10 mL of diluent; and the mixture was mixed well after 5 mm of vortex mixing. Two parts of control solutions were prepared in parallel, and labeled STD #1 and STD #2, respectively.

4. Preparation of Linear Solutions

The control solution STD #1 was taken and diluted by 1, 5, 10, 100, 1000, 2000 times, and recorded as linear solutions L1, L2, L3, L4, L5 and L6. The sample diluted by 2000 times was recorded as LOQ.

5. Experiment Results

TABLE 8

Results of solubility experiment in pH buffers and biomedia

|  | pH = 1.00 | pH = 2.00 | pH = 3.80 | pH = 4.50 | pH = 5.50 | pH = 6.00 |
|---|---|---|---|---|---|---|
| pH (24 h) | 1.11 | 1.90 | 2.61 | 4.12 | 5.26 | 5.12 |
| State (24 h) | Opalescent and opaque | Opalescent and opaque | Opalescent and opaque | White suspension | White suspension | White suspension |
| Solubility (mg/mL) _24 hr | 10.53 | 10.53 | 10.25 | 10.28 | 0.31 | 1.30 |

|  | pH = 6.80 | pH = 7.40 | $H_2O$ | SGF | FeSSIF | FaSSIF |
|---|---|---|---|---|---|---|
| pH (24 h) | 6.57 | 7.07 | 2.29 | 1.77 | 4.75 | 6.04 |
| State (24 h) | White suspension | White suspension | Opalescent and opaque | Opalescent and opaque | White suspension | White suspension |
| Solubility (mg/mL) _24 hr | 0.050 | 0.0012 | 9.12 | 10.48 | 1.32 | 0.14 |

LOQ = 0.0002515 mg/ml,

Y = 8329.2944X-1.8523, $R^2$ = 1.0000

Experimental conclusion: the solubility was described with reference to Table 9. When the crystalline form A of the compound of formula (II) was supplemented with the compound until the solubility reached 10 mg/L at pH=1.00, pH=2.00, pH=3.8, water and SGF, the solution was in a state of being opalescent; the compound had a solubility of more than 10 mg/nL at pH=1.00, pH=2.00, pH=3.8, water and SGF; the compound was minimally soluble at pH=4.50, the compound was slightly soluble at pH=6.00 and FeSSIF, the compound was very slightly soluble at pH=5.00 and FaSSIF, and the compound was almost insoluble or insoluble at pH=6.80 and pH=7.40.

TABLE 9

Description on solubility in Chinese pharmacopoeia

| Description | Solvent required by 1 g solute (mL) | Solubility (mg/mL) |
|---|---|---|
| Very easily soluble | Less than 1 | >1000 |
| Easily soluble | 1~0 | 100~1000 |
| Soluble | 10~30 | 33.3~100 |
| Minimally soluble | 30~100 | 10~33.3 |
| Slightly soluble | 100~1000 | 1~10 |
| Very slightly soluble | 1000~10,000 | 0.1~1 |
| Hardly soluble or insoluble | >10,000 | <0.1 |

Example 11: Study of Approximate Solubility

About 2.0 mg of samples were weighed and added into 1.5 mL glass vials, water was gradually added using pipetting gun, and the mixture was dissolved by sonication as appropriate. The test was conducted at room temperature and the dissolution was determined by the naked eye, and the approximate solubility results are shown in Table 10.

TABLE 10

| Test compound | Approximate solubility (mg/mL) |
|---|---|
| Compound of formula (I) | <1 |
| Crystalline form A of the compound of formula (II) | >100 |

Experimental conclusion: the approximate solubility of the crystalline form A of the compound of formula (II) in water was significantly improved compared with that of the compound of formula (I).

Example 12: Study of Solid Stability

According to the "Guidelines for the Stability Test of APIs and Preparations" (General Chapter 9001 in the Chinese Pharmacopoeia, Volume IV, 2015 Edition), the stability of the crystalline form A of the compound of formula (II) under the accelerated experiment condition was investigated. About 10 mg of the crystalline form A of the compound of formula (II) was weighed, dispersed at the bottom of glass sample bottles as a thin layer and sealed with aluminum foil, and small holes were provided in the aluminum foil. The samples were placed at (40° C./75% RH) for 2 months and 3 months and at (60° C./75% RH) for 1 month and 2 months, and the placed samples were characterized by XRPD. The test results were compared with the initial test results of 0 days. The results are shown in Table 11, and the crystal form of the crystalline form A of the compound of formula (II) is unchanged under all stability conditions.

The experiment results are shown in Table 11 below:

TABLE 11

Results of solid stability experiment of crystalline form A of the compound of formula (II)

| Conditions | Point taking conditions | Change of crystalline form |
|---|---|---|
| Initial crystalline form A | / | Crystalline form A of the compound of formula (II) |
| 40° C./75% RH | Month 2 | Crystalline form A of the compound of formula (II) |
| | Month 3 | Crystalline form A of the compound of formula (II) |
| 60° C./75% RH | Month 1 | Crystalline form A of the compound of formula (II) |
| | Month 2 | Crystalline form A of the compound of formula (II) |

Experimental conclusion: the crystalline form A of the compound of formula (II) has a good stability.

Example 13: Study of Hygroscopicity

1. Operation Process 1) two dry glass weighing bottles with stoppers (with an outer diameter of 50 mm and a height of 30 mm) were taken and placed in a drug stability test chamber (the set temperature was 25° C., and the relative humidity was 80%) for equilibration, and the weight $m_1$ of the equilibrated weighing bottles was precisely measured;

2) proper amounts of test samples were taken and spread in the two weighing bottles, wherein the test sample had a thickness of about 1 mm, and the total weight $m_2$ was precisely measured;

3) the weighing bottles were opened and placed under the constant temperature and humidity together with the bottle caps for 24 h; the weighing bottles were closed, and the total weight $m_3$ was precisely measured.

2. Calculation and Determination Basis

Calculation: weight gain $\% = (m_3 - m_2)/(m_2 - m_1) \times 100\%$

TABLE 12

Determination basis for hygroscopicity

| Description for hygroscopicity | Weight gain for hygroscopicity |
|---|---|
| Deliquescence | Absorb sufficient water to form a solution |
| Very hygroscopic | ≥15% weight gain |
| Moderately hygroscopic | 2% to 15% weight gain |
| Slightly hygroscopic | 0.2% to 2% weight gain |
| Non-hygroscopic or hardly hygroscopic | <0.2% weight gain |

3. Test Results

TABLE 13

Results of the hygroscopicity test of the crystalline form A of the compound of formula (II)

| No. | 1 | 2 |
|---|---|---|
| $m_1$ | 36397.22 mg | 30348.95 mg |
| $m_2$ | 36807.53 mg | 30767.62 mg |
| $m_3$ | 36813.02 mg | 30772.74 mg |
| Weight gain % | 1.34% | 1.22% |
| Average value | 1.3% | |
| Determination result | Slightly hygroscopic | |

Experimental conclusion: the crystalline form A of the compound of formula (II) has a slight hygroscopicity.

Test Example 1: In Vivo Pharmacokinetic Study of Crystalline Form A of Compound of Formula (II) in SD Rats

Objective

Pharmacokinetic study of the crystalline form A of the compound of formula (II) orally administered in SD rats is evaluated, and bioavailability after intragastric administration is investigated.

Procedures

The test compound was mixed with 5% dimethyl sulfoxide/10% polyoxyethylene stearate/85% aqueous solution, and the mixture was vortexed and sonicated to prepare a 3 mg/mL clear solution for later use. SD male rats aged 7 to 10 weeks were selected and orally administered with a dose of the candidate compound at 30 mg/kg. Whole blood was collected at certain time points, and plasma was separated. The drug concentration was measured by LC-MS/MS, and pharmacokinetic parameters were calculated using Phoenix WinNonlin software (Pharsight, USA).

The experimental results are shown in Table 14.

TABLE 14

Pharmacokinetic results of the test compound

| Route of administration | Pharmacokinetic parameters | Crystalline form A of the compound of formula (II) |
|---|---|---|
| Oral | Time to peak $T_{max}$ (h) | 3.0 |
| | Peak concentration $C_{max}$ (nM) | 1585 |
| | Area under plasma concentration-time curve $AUC_{0-last}$ (nM · h) | 10566 |
| | Bioavailability F (%) | 62% |

The results show that the crystalline form A of the compound of formula (II) has excellent solubility, can quickly reach a peak after 30 mpk oral administration, and has higher oral absorption bioavailability.

The invention claimed is:

1. A crystalline form of a compound of formula (II),

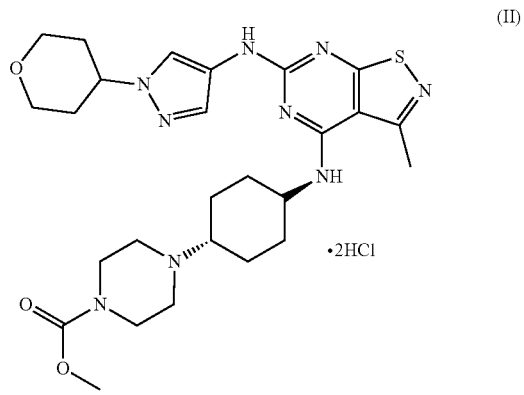

(II)

having characteristic diffraction peaks in an X-ray powder diffraction pattern using Cu Kα radiation at the following 2θ: 6.25±0.20°, 12.58±0.20°, 14.33±0.20°, 16.15±0.20°, 20.00±0.20°, 20.57±0.20°, 21.79±0.20° and 28.02±0.20°; or, having characteristic diffraction peaks in an X-ray powder diffraction pattern using Cu Kα radiation at the following 2θ: 6.25±0.20°, 16.15±0.20° and 21.79±0.20°; or, having characteristic diffraction peaks in an X-ray powder diffraction pattern using Cu Kα radiation at the following 2θ: 6.25±0.20°, 12.58±0.20°, 14.33±0.20°, 16.15±0.20°, 20.00±0.20°, 21.53±0.20° and 21.79±0.20°; or, having characteristic diffraction peaks in an X-ray powder diffraction pattern using Cu Kα radiation at the following 2θ: 6.25±0.20°, 12.58±0.20°, 14.33±0.20°, 16.15±0.20°, 20.00±0.20°, 20.57±0.20°, 21.79±0.20° and 28.02±0.20°; or, having characteristic diffraction peaks in an X-ray powder diffraction pattern using Cu Kα radiation at the following 2θ: 6.25±0.20°, 11.95±0.20°, 12.58±0.20°, 14.33±0.20°, 16.15±0.20°, 19.46±0.20°, 20.00±0.20°, 20.57±0.20°, 21.79±0.20°, 23.87±0.20°, 28.02±0.20° and 30.81±0.20°; or, having characteristic diffraction peaks in an X-ray powder diffraction pattern using Cu Kα radiation at the following 2θ: 6.25±0.20°, 8.06±0.20°, 9.29±0.20°, 11.95±0.20°, 12.58±0.20°, 14.33±0.20°, 16.15±0.20°, 16.41±0.20°, 19.46±0.20°, 20.00±0.20°, 20.57±0.20°, 21.53±0.20°, 21.79±0.20°, 27.71±0.20° and 28.02±0.20°; or, having an XRPD pattern using Cu Kα radiation at the following 2θ: 6.25±0.20°, 8.06±0.20°, 9.29±0.20°, 11.50±0.20°, 11.95±0.20°, 12.58±0.20°, 14.33±0.20°, 16.15±0.20°, 16.41±0.20°, 18.20±0.20°, 18.75±0.20°, 19.46±0.20°, 20.00±0.20°, 20.57±0.20°, 21.53±0.20°, 21.79±0.20°, 23.1±10.20°, 23.87±0.20°, 24.31±0.20°, 25.26±0.20°, 26.14±0.20°, 26.70±0.20°, 27.71±0.20°, 28.02±0.20°, 28.50±0.20°, 29.09±0.20°, 30.06±0.20°, 30.81±0.20°, 32.39±0.20°, 33.21±0.20° and 33.71±0.20°.

2. The crystalline form of the compound of formula (II) according to claim 1, having a starting point of an endothermic peak in a differential scanning calorimetry curve at 262.9±5.0° C.

3. A crystalline composition, comprising the crystalline form of the compound of formula (II) according to claim 1, wherein the crystalline form accounts for 50% or more of the weight of the crystalline composition.

4. A pharmaceutical composition, comprising a therapeutically effective amount of the crystalline form of the compound of formula (II) according to claim 1, wherein, optionally, the pharmaceutical composition comprises at least one pharmaceutically acceptable carrier or other excipients.

5. A method for treating or preventing an IRAK4-related disease, comprising administering to a mammal in need thereof a therapeutically effective amount of the crystalline form of the compound of formula (II) according to claim 1, wherein the IRAK4-related disease is inflammatory disease.

6. The crystalline form of the compound of formula (II) according to claim 1, having characteristic diffraction peaks in an X-ray powder diffraction pattern using Cu Kα radiation at the following 2θ:

| No. | 2θ (°) | Interplanar spacing (Å) | Relative intensity (%) |
| --- | --- | --- | --- |
| 1 | 6.25 | 14.15 | 51.54 |
| 2 | 8.06 | 10.97 | 4.42 |
| 3 | 9.29 | 9.52 | 1.53 |
| 4 | 11.50 | 7.69 | 6.83 |
| 5 | 11.95 | 7.40 | 19.50 |
| 6 | 12.58 | 7.04 | 39.24 |
| 7 | 14.33 | 6.18 | 39.55 |
| 8 | 16.15 | 5.49 | 44.87 |
| 9 | 16.41 | 5.40 | 25.16 |
| 10 | 18.20 | 4.88 | 11.79 |
| 11 | 18.75 | 4.73 | 12.07 |
| 12 | 19.46 | 4.56 | 26.74 |
| 13 | 20.00 | 4.44 | 43.30 |
| 14 | 20.57 | 4.32 | 36.44 |
| 15 | 21.53 | 4.13 | 49.75 |
| 16 | 21.79 | 4.08 | 100.00 |
| 17 | 23.11 | 3.85 | 12.56 |
| 18 | 23.87 | 3.73 | 16.00 |
| 19 | 24.31 | 3.66 | 15.05 |
| 20 | 25.26 | 3.53 | 11.31 |
| 21 | 26.14 | 3.41 | 12.82 |
| 22 | 26.70 | 3.34 | 8.25 |
| 23 | 27.71 | 3.22 | 20.94 |
| 24 | 28.02 | 3.19 | 27.89 |
| 25 | 28.50 | 3.13 | 13.41 |
| 26 | 29.09 | 3.07 | 9.69 |
| 27 | 30.06 | 2.97 | 12.97 |
| 28 | 30.81 | 2.90 | 18.47 |
| 29 | 32.39 | 2.76 | 5.96 |
| 30 | 33.21 | 2.70 | 10.22 |
| 31 | 33.71 | 2.66 | 6.58 |
| 32 | 34.55 | 2.60 | 6.59 |
| 33 | 36.43 | 2.47 | 3.25. |

* * * * *